(12) United States Patent
Lee et al.

(10) Patent No.: US 7,016,721 B2
(45) Date of Patent: Mar. 21, 2006

(54) MEDICAL DEVICE ECG MARKER FOR USE IN COMPRESSED DATA STREAM

(75) Inventors: Brian B. Lee, Golden Valley, MN (US); Michael R. Kane, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 326 days.

(21) Appl. No.: 09/975,621

(22) Filed: Oct. 10, 2001

(65) Prior Publication Data

US 2002/0026122 A1 Feb. 28, 2002

Related U.S. Application Data

(62) Division of application No. 09/353,277, filed on Jul. 14, 1999, now Pat. No. 6,347,245.

(51) Int. Cl.
*A61B 5/0432* (2006.01)

(52) U.S. Cl. .................. 600/523; 607/27; 607/30
(58) Field of Classification Search .................. 600/523, 600/509, 510, 521, 519; 607/27, 28, 59, 30
See application file for complete search history.

(56) References Cited

U.S. PATENT DOCUMENTS

| | | | |
|---|---|---|---|
| 4,223,678 A | | 9/1980 | Langer et al. |
| 4,407,288 A | | 10/1983 | Langer et al. |
| 4,556,063 A | | 12/1985 | Thompson et al. |
| 4,712,556 A | * | 12/1987 | Baker, Jr. .................. 607/14 |
| 4,969,467 A | * | 11/1990 | Callaghan et al. ............ 607/28 |
| 5,313,953 A | | 5/1994 | Yomtov et al. |
| 5,331,966 A | | 7/1994 | Bennett et al. |
| 5,339,824 A | | 8/1994 | Engira |
| 5,404,887 A | | 4/1995 | Prather |
| 5,464,431 A | | 11/1995 | Adams et al. |
| 5,464,434 A | | 11/1995 | Alt |
| 5,518,001 A | | 5/1996 | Snell |
| 5,908,392 A | * | 6/1999 | Wilson et al. ............... 600/509 |
| 6,301,503 B1 | * | 10/2001 | Hsu et al. ..................... 607/30 |

OTHER PUBLICATIONS

Lee et al., "Subcutaneous, Bipolar "Pseudo–ECG" Recordings Using an Implantable Monitoring System", NASPE Abstracts, 321, Pace, vol. 15, part II, Apr. 1992.

* cited by examiner

*Primary Examiner*—George R. Evanisko
(74) *Attorney, Agent, or Firm*—Paul H. McDowall; Girma Wolde-Michael

(57) ABSTRACT

Triggers and noise should be available as information in recorded electrograms in memories of implantable medical devices. Particularly where the recording of electrogram data is done in the far field, there will be considerable noise and the interpretation of ECG's reproduced from such recorded data will benefit from the storing of information regarding contemporaneous noise. By storing contemporaneous trigger data and noise data directly in the ECG data, recordings of the ECG data become more useful for physician use when played back through an external display system with minimal loss of ECG data, since out of range values are employed for the noise and trigger information and this non-ECG data is limited in size to no longer than individual point values of the ECG signal.

41 Claims, 17 Drawing Sheets

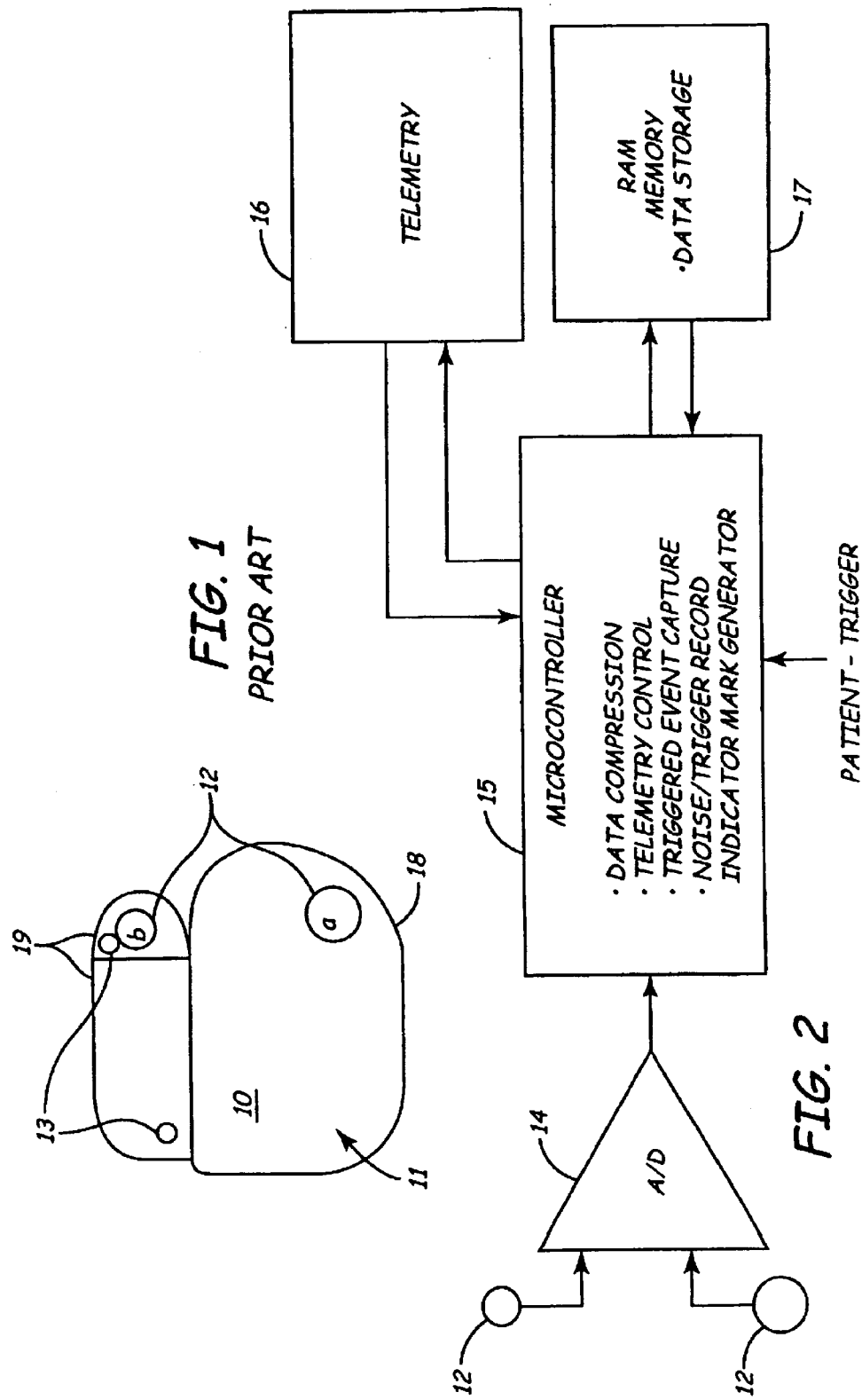

△=ACTIVATION POINT

MEDICAL DEVICE ECG MARKER FOR USE IN COMPRESSED DATA STREAM

This application is a divisional application of application Ser. No. 09/353,277, filed Jul. 14, 1999 now U.S. Pat. No. 6,347,245.

This invention relates to an implantable monitoring device having capability for sensing and/or recording physiologic events, preferably with minimally invasive intrusion into an animal or patient body, but which can be used with various implantable devices that provide long term monitoring of electrocardiograms (ECG's). More particularly this invention relates to how to indicate what kind of interfering noise is present during recording or whether and what type of auto activation sequence was present caused a particular segment of ECG to be recorded and how to simply and appropriately add such data to a compressed data stream. Thus, this invention also relates to how to enable easier interpretation of data stored contemporaneously with an apparent physiologically significant event.

BACKGROUND OF THE INVENTION

In using implantable medical devices for recording ECG's or other physiologic data, the data available when the record is made can be useful in interpreting the saved signal records. Various things like the fact of occurrence or nature of the automatic trigger that activated storage of data, and the noise present when the record is made can be invaluable in sorting out the data record to eliminate false indications of medical conditions and discover actual problems which would otherwise remain hidden in the data or lost forever. Triggers and noise should be available as information in recorded electrograms in memories of implantable medical devices. Particularly where the recording of electrogram data is done in the far field, there will be considerable noise and the interpretation of ECG's reproduced from such recorded data will benefit from the storing of information regarding contemporaneous noise. Thus we believe it will be extremely beneficial to the practice of medicine and to medical research if contemporaneous trigger data and noise data could be stored directly in the ECG data, which could them be played back through an external display system with minimal loss of ECG data. The confusion of data by physiologic signals other than the ECG and with the trigger information can be problematic. It becomes even more problematic and detrimental to the data record in the context of desires to store implantable medical device system data, and to achieve a good reproduction of actual physiologic signal data at the same time, with complexities arising from compression needs and limited bandwidth and time to maintain telemetric contact with the implantable device, which is further limited by its limited battery capacity to short communication sessions at low power or slow speeds.

In the monitoring of long term ECGs for features indicating intermittent heart irregularities, syncopal events and the like, minimally invasive monitors like the Reveal (TM) electrocardiogram event recorder manufactured by Medtronic, Inc. have proven to be useful, and now appear to be accepted by a segment of the medical community for use in diagnosing patient problems like fainting. However, particularly when the device employs automatic arrhythmia detection triggers to activate the storage of a segment of the ECG, the presence of noise in the ECG signal channel may trigger activations of recordings inappropriately, causing the device memory to become full of unwanted or redundant portions of the cardiac electrogram which may be of little to no use in diagnosing the patient condition Also, such noise when present may show up as a noisy signal in the recorded data, making interpretation of the signal and, diagnosis based on such interpretation, difficult.

It is felt that if the reconstituted electrogram read out for the physician had markers for identifying the type of noise present or the particular kind of trigger that caused the electrogram segment to be recorded, then the interpretation of even a noisy ECG would be easier and more accurate.

However, in order to store such information regarding the kind of noise or the nature of the auto-trigger or both, it might be thought that a separate memory or at least a separate location in memory from the ECG storage area would be required, along with a way to identify which marker was associated with any given segment of ECG data storage.

An additional complexity can be found in the limitation on the nature of the data available to store electrogram data samples, especially when, for one example, the sample rate produces more electrogram features than are stored via a lossy data compression technique in long term monitoring devices, a process relied upon to save memory and achieve sufficient data storage capacity to assist the physician in evaluating a long term ECG.

Accordingly we have developed a method and apparatus for identifying information available to an implantable medical device in an ECG data storage memory area which accommodates of the nature of the data compression and data communication requirements of the medical device.

Monitoring can be done using implantable pulse generators such as pacemakers and other heart stimulating devices or devices with leads in the heart for capturing physiologic parameters, including the ECG. However, the expense and risk from implanting a pacemaker or changing out one without these functions is something both patients and physicians would prefer to avoid. Such devices, in addition to performing therapeutic operations, may monitor and transmit cardiac electrical signals (e.g., intracardiac electrograms) to external diagnostic devices typically with leads fixed in the patient's heart, to observe electrical activity of a heart. It is common for implanted cardiac stimulation devices to send intracardiac ECG signals to a monitoring device, such as an external programmer, to allow a user to analyze the interaction between the heart and the implanted device. Often the user can designate that the communication from the implantable device to the programmer include a transmission of codes which signal the occurrence of a cardiac event such as the delivery of a stimulation pulse or a spontaneous cardiac depolarization.

For example, U.S. Pat. No. 4,223,678, (incorporated herein by this reference in its entirety) entitled "Arrhythmia Recorder for Use with an Implantable Defibrillator", issued to Langer et al. on Sep. 23, 1980, discloses an arrhythmia record/playback component within an implantable defibrillator. ECG data is converted from analog to digital (A/D) form and stored in a first-in, first-out memory. When the defibrillator detects an arrhythmia event, it disables the memory so that no further ECG data is recorded in the memory until a command is received from an external monitoring device. This command requests the implantable defibrillator to transmit the stored ECG data to the monitoring device via telemetry. Langer et al. in U.S. Pat. No. 4,407,288, (also incorporated by reference herein) entitled "Implantable Heart Stimulator and Stimulation Method", issued Oct. 4, 1983, discloses a programmable, microprocessor based implantable defibrillator which senses and loads ECG data into a memory via a direct memory access operation. A processor analyzes this ECG data in the memory to detect the occurrence of an arrhythmia event afflicting a patient's heart. Upon such an event, the defibrillator may generate a therapy to terminate the arrhythmia event and store the ECG data sequence of the event, for transmission to an external monitoring device and later study. In normal circumstances, when no arrhythmia event is occurring, the defibrillator continuously overwrites the ECG data in the memory.

U.S. Pat. No. 4,556,063, (too, incorporated herein by this reference) entitled "Telemetry System for a Medical Device", granted to D. L. Thompson et al, 1985, teaches a pulse interval telemetry system capable of transmitting analog data, such as sensed intracardiac electrogram signals, without converting analog data to a digital numeric value. The Thompson et al. telemetry system is capable of sequentially transmitting both digital and analog data, individually and serially, in either an analog or a digital format, to a remote receiver. The features and capabilities of these pacemaker/defibrillator devices is now well known, but the problems in long term monitoring for events and adequate recordation and interpretations of noisy excessively triggered records remain.

Other background includes an article in the December 1992 Vol. 15 edition of PACE (15:588), a feasibility study for implantable arrhythmia monitors and reported by Leitch et al. Subcutaneous, Bipolar "Pseudo-ECG" Recordings using an Implantable Monitoring System and at chaired poster presentation of the North American Society of Pacing and Electrophysiology (NASPE).

Further, a leadless implantable sensor for cardiac emergency warning was described in U.S. Pat. No 5,404,887 issued to Knowlan et al. which detects heart events through impedance measurement sensed using a coil. See also Yomtov et al, U.S. Pat. No. 5,313,953 (incorporated herein by this reference) which describes (in FIG. 26) a large but leadless implant.

With sufficient hardware and connections to the body, numerous other physiologic parameters may be sensed as is pointed out in U.S. Pat. No. 5,464,434 issued to Alt and U.S. Pat. No. 5,464,431 issued to Adams et al. (both also incorporated herein by this reference).

Nevertheless there is still a need to indicate what kind of noise is present in a particular ECG segment and to do so in an efficient manner within the constraints imposed by the limitations of inexpensive devices with limited communications capacity, limited battery strength and limited time to communicate, and limited memory capacity, especially where the signal stored in memory may be complicated with data compression.

Of course, there is substantially more data that would be useful to capture along with the noise, including other physiologic condition sensor data, apparent R-waves which may be used for the arrhythmia triggers, indications of losing contact with the body by the electrodes, detecting pacing pulses, defibrillation pulses, low battery and other internal to the device conditions and so on. All such data may be substituted for interchangeably in various preferred embodiments of the present invention.

Presently without some indication of what kind of interfering or influencing signals are present, especially in situations where the ECG is reconstructed from a compressed electrogram storage, it is difficult to interpret the reconstructed ECG display.

The kinds of influences include ElectroMyoGraphic (EMG) noise from muscle activity, artifact noise from electrode motion within the body, loss or change in the electrode/body contact, pacemaker pulses, defibrillator pulses, and Electro-Magnetic Interference (EMI), which can be of a wide variety of types from different sources.

In addition it may be difficult to interpret the reason an automatic arrhythmia detection process chose to record the ECG segment being studied in the presence of such interfering signals, or in the absence of some interfering signals where filtering techniques or other anti-noise responses have eliminated much of the noise signal itself. It is not easy to answer the question: "Was the trigger set off by the noise, or not?", and yet it is important for a valid diagnosis, to be able to do so. Too, with subcutaneous, or far field electrodes, ECG signal amplitude may vary greatly with mere change in patient posture; therefore knowing whether the recorded signal is a real arrhythmia or an artifact of poor detection performance is very difficult without real time information about the conditions present when the ECG sample was taken.

One final complication may arise where an ECG segment can be recorded by a patient controlled activation device. There needs to be room enough to recognize this extra signal and reason for recording the electrogram.

BRIEF DESCRIPTION OF THE DRAWINGS

FIG. 1 is an exterior side view of a prior art device.

FIG. 2 is a block diagram of parts of an implantable medical device for use with a preferred embodiment.

SUMMARY OF THE INVENTION

Figure 3:
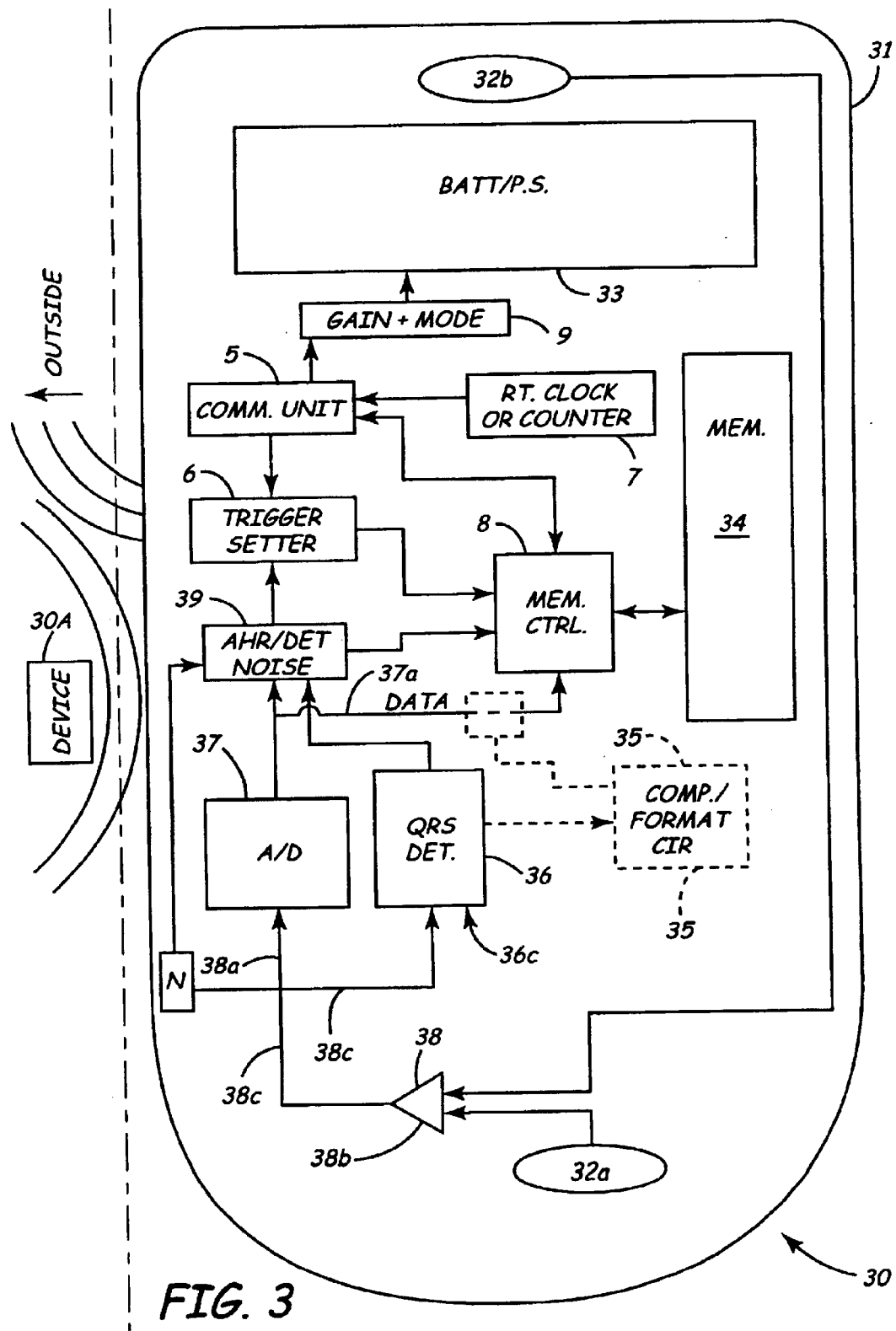
FIG. 3 is a block diagram illustrating the main circuit and assembly of a device in accord with a preferred embodiment.

We describe in various configurations a system, apparatus and/or method for relaying real time information about conditions that exist contemporaneously with the recording of an ECG signal. We provide details regarding how to record either the trigger reasons for initiation of recording of an ECG segment, or of physiologic or noise condition information contemporaneous with the ECG recording. We also describe the relaying of such information in the ECG data.

During recording of segments of ECG's, a variety of information is lost in the normal use of subcutaneous (and other) ECG monitors. This information can be made available, which provide invaluable interpretation of the reconstituted ECG signal when viewed on a physician's screen or electrocardiogram tape.

Since R-waves are often used to trip automatic triggers, it is of particular importance in devices having such automatic triggers to record of contemporaneous noise which may have in fact tripped the trigger, or conversely, which may obscure the ECG display. (It is of course possible to exclude many forms of noise from the signal being recorded or from forcing activation of a trigger, but that is not related to this invention. For the purposes of this invention the most relevant noise will be that which causes difficulties in interpretation of a signal, not that which can be successfully filtered out. It is possible, in the context of our invention, to use the fact that a given pulse has been identified as noise to logically reject such a pulse in the high level arrhythmia detection logic that may be used to automatically trigger an electrogram storage period). Another important kind of indicator that could be marked on the display of the ECG is an indication of the type of trigger that caused the recording. Was it manual or automatic? Was it a Bradycardia event or a Tachycardia event or an Asystole that caused the auto-trigger? Answers to these questions that may be indicated on the electrogram display can indicate whether the data that the device is working with is any good, or whether the device itself is working properly, as well as providing some redundancy to the visual examination of the reconstructed snippet of electrogram, recorded and compressed by the implantable device, possibly months earlier.

The kinds of noise that may show up in the electrogram include at least noise caused by Electronic Article Surveillance (EAS), ElectroMagnetic Interference (EMI) noise, ElectroMyographic (EMG) noise, spurious electrode/tissue movement, pacing spikes, defibrillator spikes, and so forth. A series of filters or filter taps can be used, together with digital signal processing if desired, to determine the nature of these noise signals as they are occurring.

The noise is categorized in preferred embodiments by using knowledge about the temporal frequency characteristics of the noise. For example, EMG noise is broad band and can be characterized by broadband filters. As another example pacing and defibrillator spikes are generally high voltage and current and of regularized or expected duration. EMI is generally high frequency and appears in bursts.

Further, if the device has information about other indications of physiologic condition which either contributed to the tripping of the auto-trigger or occurred contemporaneously with the tripping of the trigger, whether the trigger is manually activated or automatic, such information can provide useful clues to the causes of the electrogram reading the way it may read, and the subsequent diagnosis of patient condition. The background art provides a wide variety of useful adjunct sensors including sensors for edema, pressure, temperature, cardiac output, blood flow, Oxygen saturation of the blood, pH, ischemia in the heart, motion or activity, and other sensors that may be useful. The combining of contemporaneous information from such sensors with triggered electrograms is also taught herein. It should also be noted that the data can be stored in parallel if desires such that two memory buffers can be filled, one with the ECG data and one with the sensor data, if desired. This could be particularly advantageous for a pressure wave signal for example.

The information that is found in real time while the ECG signal is being monitored, in our preferred embodiment, is stored in the ECG memory area as a set of coded markers within the data itself, replacing data points in the compressed and sampled signal with a value set to off-limit values. In the system for retrieval of the ECG segment for display, an interpretive processor in the external device provides an indicator marker in the electrogram where the trigger occurred or where the measurement of the sensor took place. In the compressed data, this may affect the usability of the data stream to produce best possible quality ECG output, but the value of the information contained should more than offset this information loss. The interpretive processor can complete the ECG display with intelligence if desired, or not, if preferred.

Certainly, if noise is found in the input signal, the device can respond by eliminating R-wave detection signals or by modifying the patterns of acceptable auto trigger responses to apparent R-waves in the presence of noise, which may affect which segments of the ECG will be recorded. In such cases, no data may be stored if the trigger is not tripped.

DETAILED DESCRIPTION OF THE PREFERRED EMBODIMENT

Prior to Medtronic Reveal(™) implantable ECG monitor, the only consistent use of implantable electrode sensing systems employed leads located in the heart because of the quality of the signal obtained that way. Subcutaneous electrodes (below the skin, producing a far field electrocardiogram as compared to the intracardiac ECG available through most implantable devices today) have thus only recently been demonstrated to be effective in producing good monitoring devices, and have not yet found large scale commercial medical success. A well known example of a system having leads which also contained more than a single electrical contact in the body of the pacemaker was described in U.S. Pat. No. 5,331,966 issued to Bennett et al. in 1994, and incorporated herein by this reference. In column 8 of that patent, several other implantable recording systems are described.

Particularly in non-therapeutic devices that merely record physiologic conditions into the physiologically relatively noisy environment of the subcutaneous region, data regarding noise and auto-trigger becomes more important.

An early implantable device is described with reference to FIG. 1 and which appeared at a NASPE (North American Society of Pacing and Electrophysiology) conference as a poster presentation in 1994. The device 10 was provided with two suture holes 13 and two spaced apart non-lead or leadless electrodes 12 at one and one-quarter inches distance center to center. The device was coated with paralene indicated by arrow 11 so that the only area of exposure on the body of the pacer can 19 is the exposed area at the electrode 12a. The other electrode is a metal plug electrode 12b mounted in a connector block 19.

In FIG. 2 the same electrodes 12 supplied signals into the circuitry inside the housing or "can" 18 (FIG. 1) by first entering a analog to digital conversion and amplifier circuit 14. Data from this circuit 14 was fed to a microcontroller 15 which provided functions of data compression, telemetry control and event capture triggered by patient operation. Telemetry block 16 and RAM memory storage 17 were also provided in this device.

Refer now to FIG. 3 in which a circuit block model 30 is illustrated in an outline of an implantable device which can be used with this invention; having a shell 31. Electrodes 32a and 32b bring signal from the body to an input mechanism 38, here drawn as a differential amplifier for simplicity only, the output of which is fed to a QRS detector 36 and an A/D converter 37. Both these circuits 36 and 37 may supply output to an arrhythmia/noise detector 39, which in this preferred embodiment supplies the auto-trigger signal to the trigger setting circuit 6. The data output from the Analog to Digital converter may be converted, compressed, formatted and marked or reformulated if desired in a circuit 35 before the data is ready for input into the memory 34. The Memory control circuits 8 receives input from the A/D converter, with or without conversion and so forth from circuit 35, from the auto-triggering determination circuit (here seen as the arrhythmia/noise detection circuit) 39 (which may include input directly from the QRS detector if desired) as well as signals from the trigger setter circuit 6. (We may use the terms auto-triggering and auto-activation and auto-detection interchangeably. They all refer to the action of storing information in memory based on an automatic response to a change in a measured parameter or count or algorithmic process determination). The memory controller circuit may compress the electrogram data, preferably using a variation of the turning point algorithm of U.S. Pat. No. 5,331,966 incorporated herein by reference, although any compression technique may be employed for storing the ECG to memory. The trigger setter circuit may also be controlled by a communications unit 5 which operates to receive and decode signals from outside of the implant 30 that are telemetered or otherwise communicated in by a user. This communications unit 5 will also be able to communicate with the memory controller to request the off-loading of memory data for analysis by an outside device. It should contain an antenna or other transceiver device or circuitry to communicate with an outside device such as device 30A. A clock or counter circuit 7 reports the time since start, or real time, to the outside interrogator device 30A contemporaneously with a data off-loading session so that the events recorded in memory 34 may be temporally pinpointed.

Alternatives to this overall design may be considered, for example by using a microprocessor to accomplish some or all of the functions of circuits 6,8, 39, and 35 but it is believed that such a design will not provide the power and size savings taught by use of the preferred design. See FIG. 4 and accompanying description below for a microprocessor driven version.

Figure 4:
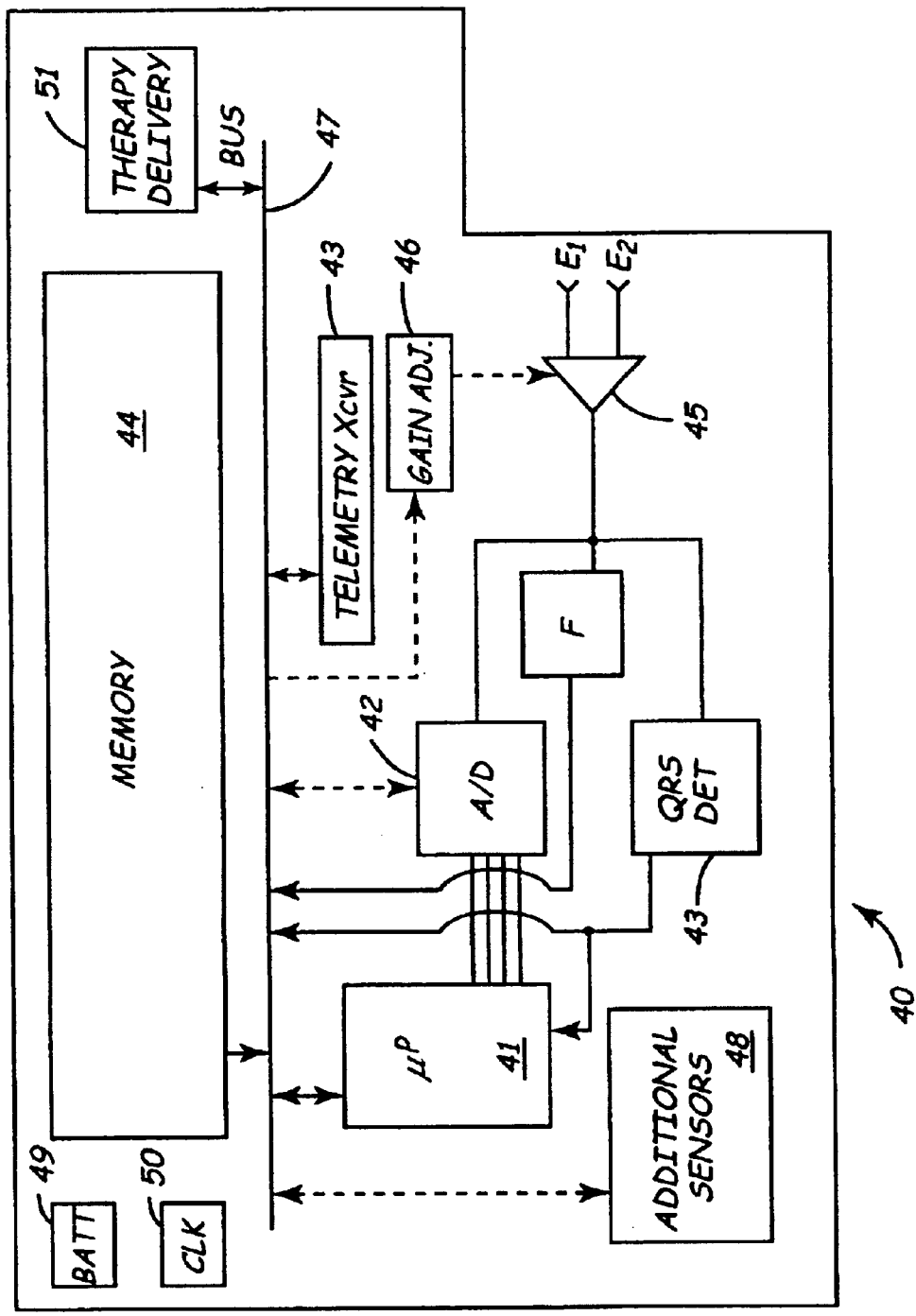
FIG. 4 is a block circuit diagram of an alternative embodiment to that illustrated in FIG. 3.
Figure 4C:
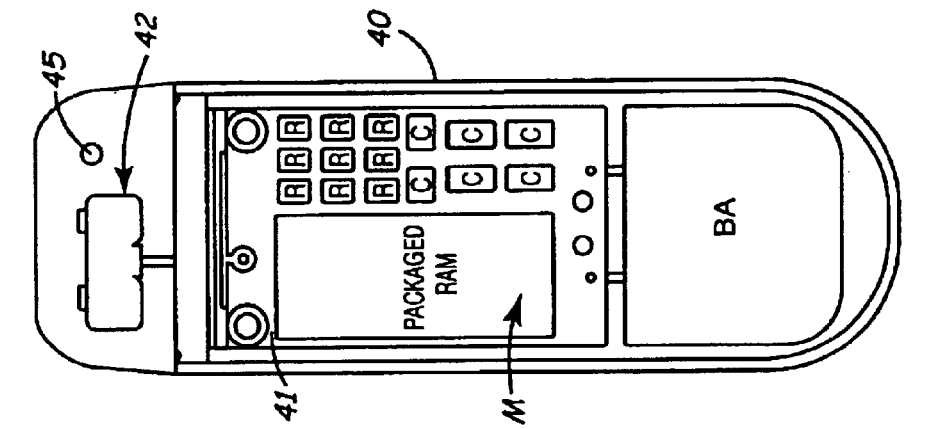
Figure 4B:
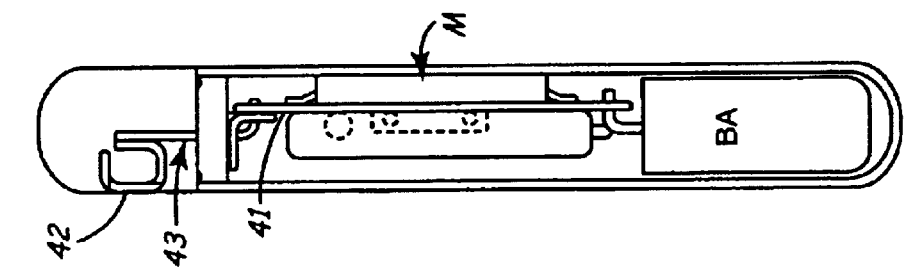
Figure 4A:
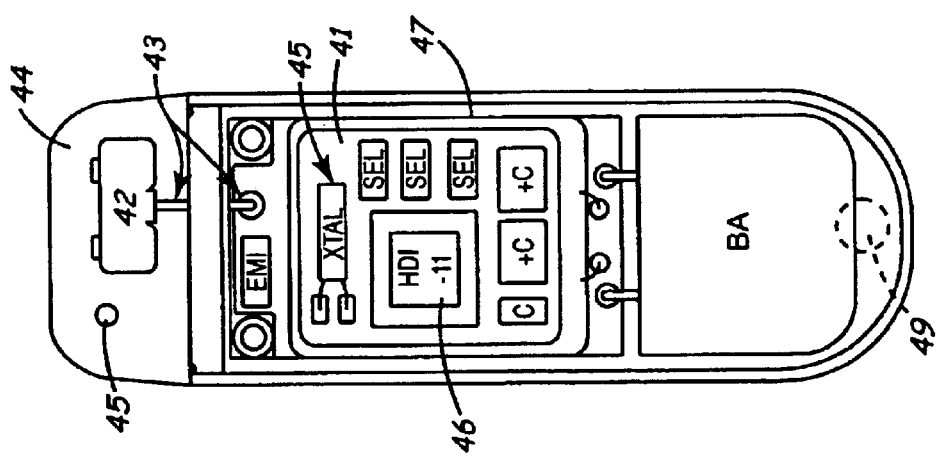

FIGS. 4A–C illustrate one preferred form 4 of the invention. In this form it has an outer titanium shell 40, in a plastic cap means 44, which together form the exterior of the device. The cap means 44 may be composed of material similar to those used for pacemaker connector blocks as it is in the is case. The two electrodes, 44 and 49, provide metal surface contacts to the body. Electrode 49 is formed as a whole in a paralene coating over the metal body 40, of the device. The metal electrode 42 is connected via a feedthrough 43 which is itself electrically connected to the circuit board 41. Circuit board 41 contains all the electronics required for the device function and is connected to a battery BA for power. An integrated circuit 46 houses circuitry and intelligence required for the function and the memory M is packaged on the other side of the circuit board. In this preferred form, the invention uses a communications circuit 45 having a telemetry antenna both to indicate from outside the body that a read out is requested of the device, and for communicating data out from said device. Programming of the device or mode setting will also use the communications circuit 45. In this form also one or more suture holes 45 is or may be provided through the cap means 44. Electrode 49 is connected by a conductive connection (not shown in this FIG.) to the circuit board. In this embodiment the length "l" is substantially longer than the width "w". These measurements can be varied within the constraints described.

The exact sites of implant may advantageously be varied from patient to patient for various reasons apparent to the physician. Implant just under the skin now may provide a signal that is most free of skeletal muscle myopotential or body movement signal interference.

Referring again to FIG. 3, the external device 30A is preferably a device that is commonly called a "programmer" in the pacemaker art, because its usual function is to communicate with and program implanted devices. Software modifications and modifications to the telemetry system of device 30A to accommodate communication with and analysis of data from device 30 can be made as required. Such modifications will vary with the programmer type and are within the discretion of the manufacturer and thus will not be illustrated here. Using a programmer will avoid having to have additional devices cluttering the operating room or clinic by creating a separate and distinct external communications device for this invention. The functionality necessary for mere ECG monitoring and event triggering is minimal, so in the preferred embodiments that only monitor some form of ECG or other limited sensory input, a microprocessor can be and is done away with altogether by using particularized functional circuits instead of doing the functions in software.

In FIG. 4, an alternative form of the implantable monitoring device 40 is illustrated, receiving input from two electrodes $E_1$ $E_2$ into an input amplifier 45. The output of the input amplifiers analog to digital converted in AID circuit 42 providing an input data stream to the microprocessor 41. Additionally, a QRS detection circuit 43 monitors the analog output of amplifiers circuit 45 providing an output signal to either the micro processor 41 or the bus 47 as desired. In this simplified device 40 in this schematic of FIG. 4, the bus 47 will provide a data conduit for enabling and disabling functions of all circuits to which may be attached and for the transmission of data between the various circuits components and elements of the device 40. A telemetry transceiver 43 and memory circuit 44 will be able to move large amounts of data in a convenient way along this data conduit bus 47 as required for the operation of the system. A data compression circuit may preferably be included as part of the A/D circuit. Additional sensor circuits 48 may also provide data to the various circuits through the bus 47. Information from the additional sensor circuits, the QRS detector, or the A/D output itself can be processed by the microprocessor to determined if the ECG contains particular kinds of noise. Alternatively, with the addition of a filter and characterization circuit F, the device can tap the analog input (either before or after the amplifier, depending on whatever filtering might be inherent in the electrode to amplifier pathways), to process frequency, duration and amplitude characteristics inductive of particular kinds of noise. The evaluation made by filter and characterization circuit F circuit will preferably be provided as an output in the form of a coded instruction to the microprocessor so that it can be added as an appropriate value to the stored electrogram segments when the instruction is received by the microprocessor (and may also be used as an input to help improve arrhythmia detection accuracy). Alternatively it could just be passed on to a compression and storage circuit if the ECG signal is provided to the memory through such a route.

A battery should be provided or other power circuit 49, and a clock circuit 50 would also be necessary to coordinate the transmission of data between the various circuit components and time their functions.

Additionally, if desired, a therapy delivery circuit 51 may provide additional functions for the implanted medical monitoring device so that the device may take advantage of the data being gathered to deliver a particular therapy of use to the patient in a timely manner.

It is believed to be most convenient to describe how the data is produced from the input signal with respect to the most preferred embodiment. However, it is also believed to be within the ambit of this invention to modify the following circuits for use with alternative embodiments such as the ones that may rely on a micro processor controller circuit as in FIG. 4.

Figure 3A:
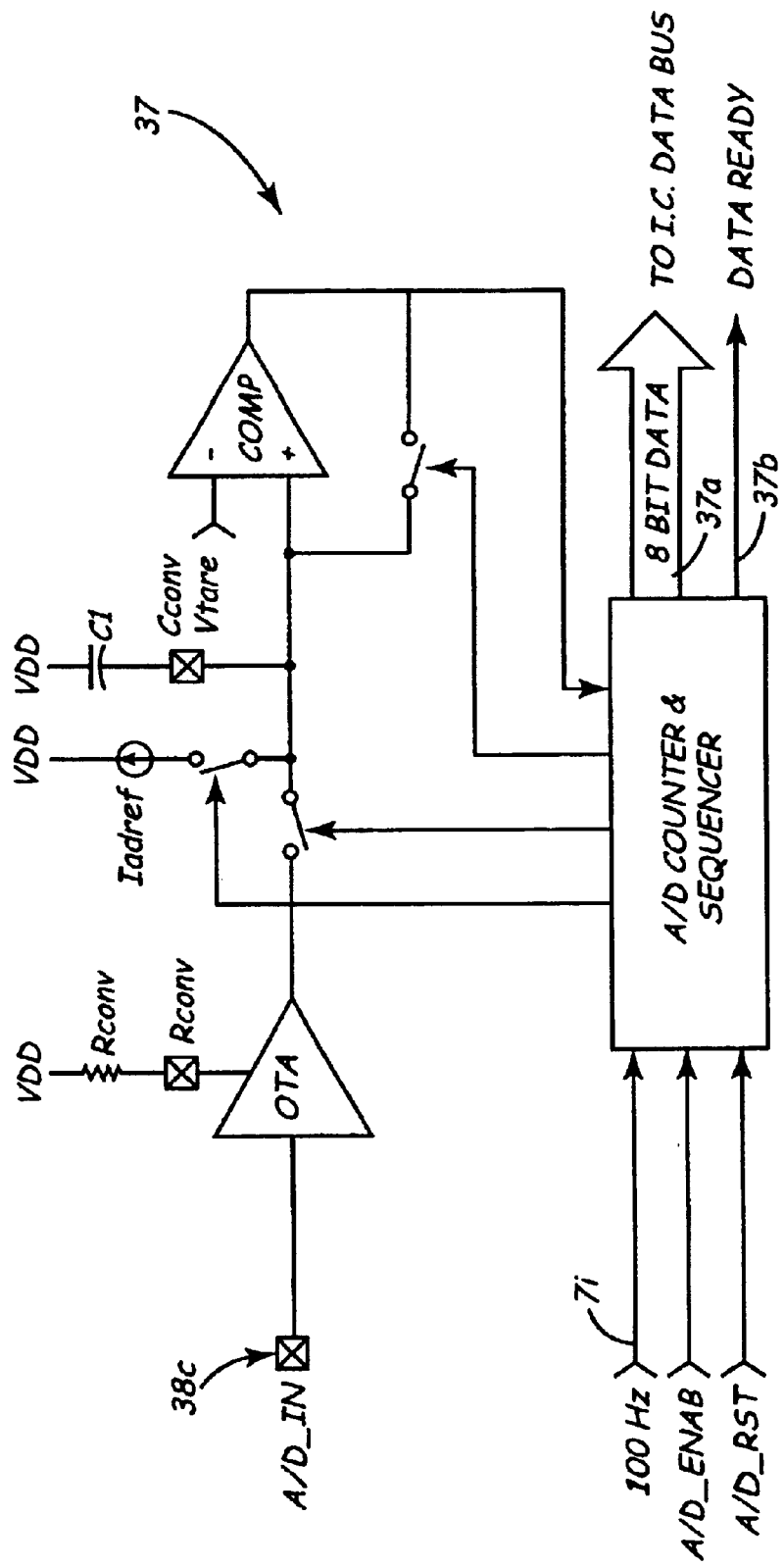
FIGS. 3A–D are block diagrams of preferred embodiment circuits of the implanted device used for monitoring and storing ECG's.

In FIG. 3A, a block diagram of an analog to digital conversion circuit for use in this invention is shown. The clock input may advantageously use an output from the clock circuit 7, input 7i. The input 38c is the analog input signal from input circuit 38, and the converted output is a stream of 8 bit digital data words on line 37a, sequenced by a timing line 37b.

Figure 3B:
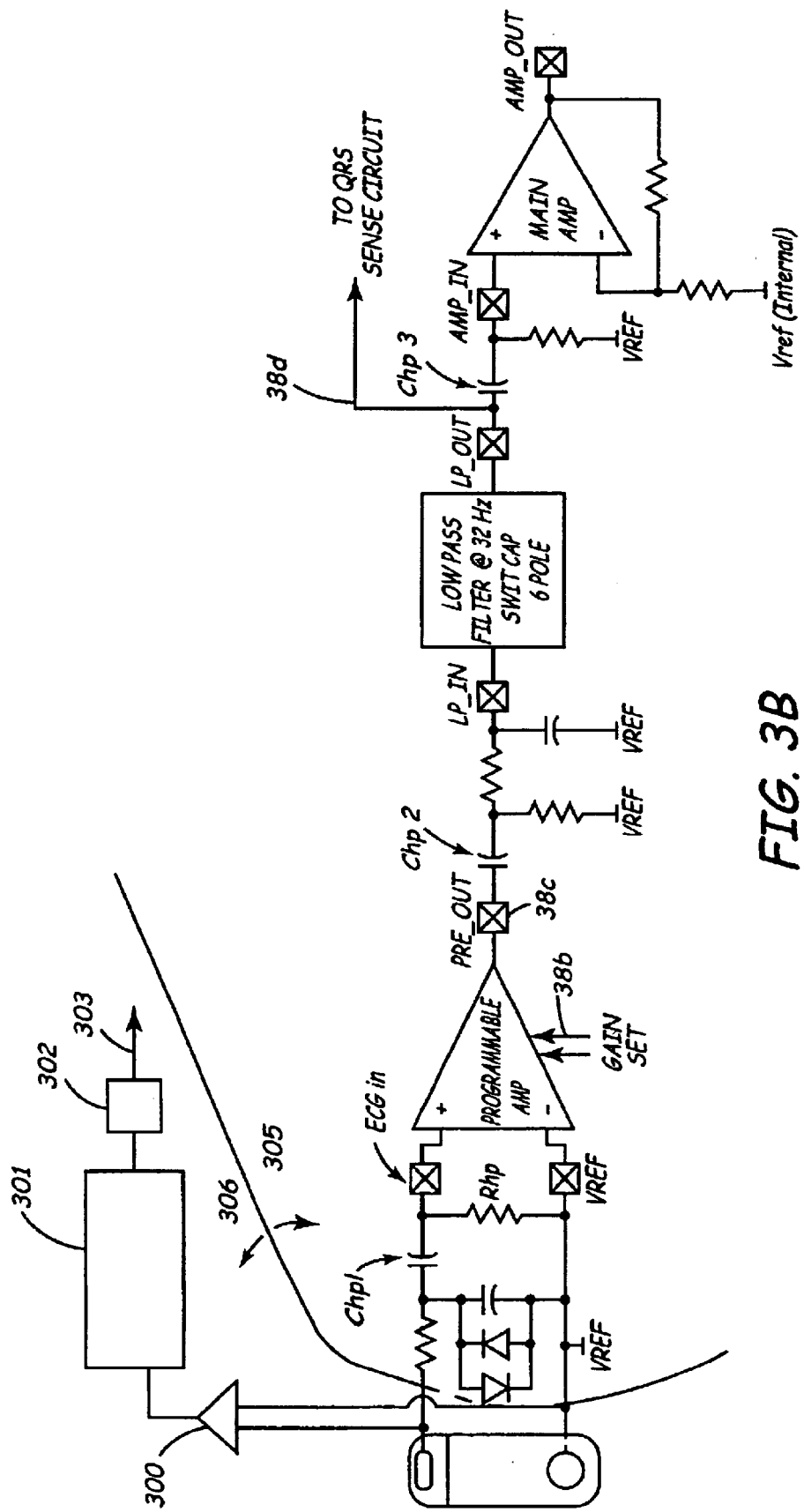

FIG. 3B illustrates the basic parts of circuit 38, additionally indicating the input of two gain set bits which can modify the value of the output of the low noise bipolar amplifier for output at line 38c, which after filtering will provide the input to the QRS detector at 38d. In this invention QRS detection is done on the analog signal, advantageously avoiding more complex detection required after digital conversion for the triggering of event storage. Importantly, although we here illustrate the preferred embodiment plan of tapping the signal directly from the electrodes to amplifier 300 for determining what kind of noise might be in the signal, it should be noted that at any stage in the process of producing an output for the QRS detector (38d) or even at the AMP_OUT stage, one could tap off the signal to generate an indication of a particular kind of noise. For example, at the AMP_OUT stage, one could detect pacing spikes, but not most defibrillation pulses, and the EAS and EMI noise signals would likely be lost in the low pass filter 304. Accordingly, since the main path 305 of this circuit 310 is for determining valid QRS signals and providing ECG amplitude values for conversion to digital signals for compression and storage, the alternative path 306 is a preferred approach. In path 306 the signal will be filtered and analyzed appropriately to the particular kinds of noise the device seeks to mark in box 301, and the output will be collected and digitized in box 302 for processing and storage, preferably in the electrogram or ECG signal storage area of the memory.

Figure 3C:
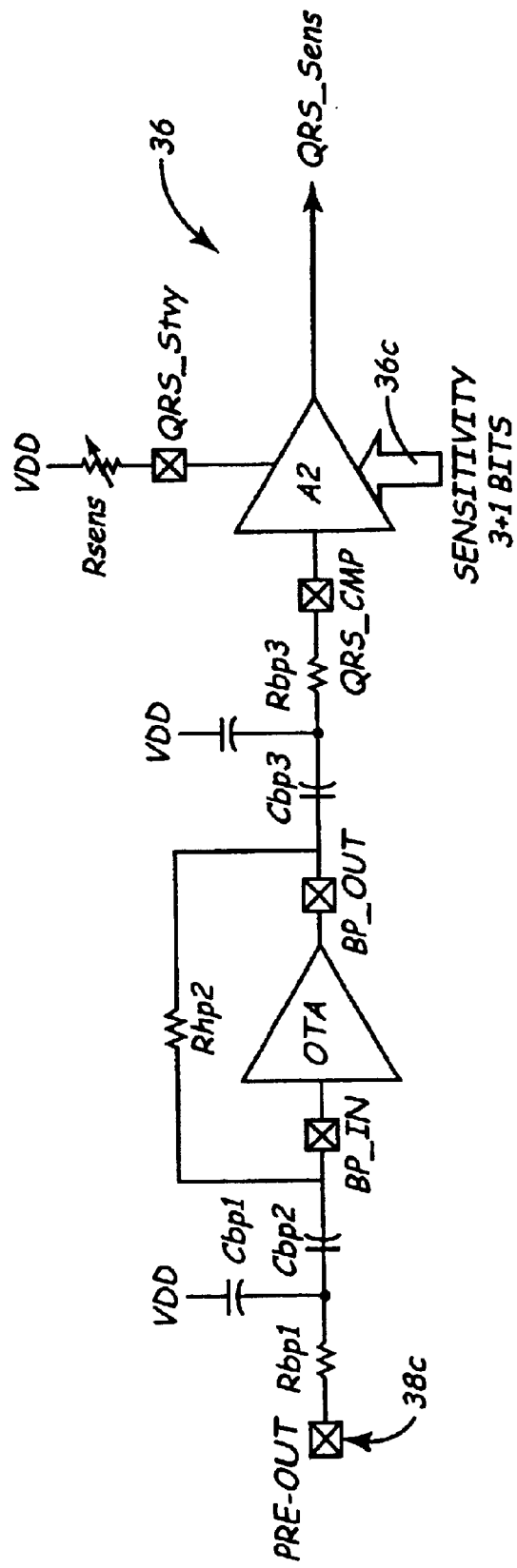

In FIG. 3C, QRS detect circuit 36 has a 2nd order bandpass filter with a center frequency preferably in the 20–25 Hz range. It includes a transconductance amp A1, summing amp/comparitor A2 and resistors Rbp1–3, capacitors Cbp1–4 and selectable resistor R sense connected as shown. R sense is preferably adjusted during manufacture. Additional control is provided for QRS sensitivity at line 36c, since the gain is detectable for this input.

Figure 3D:
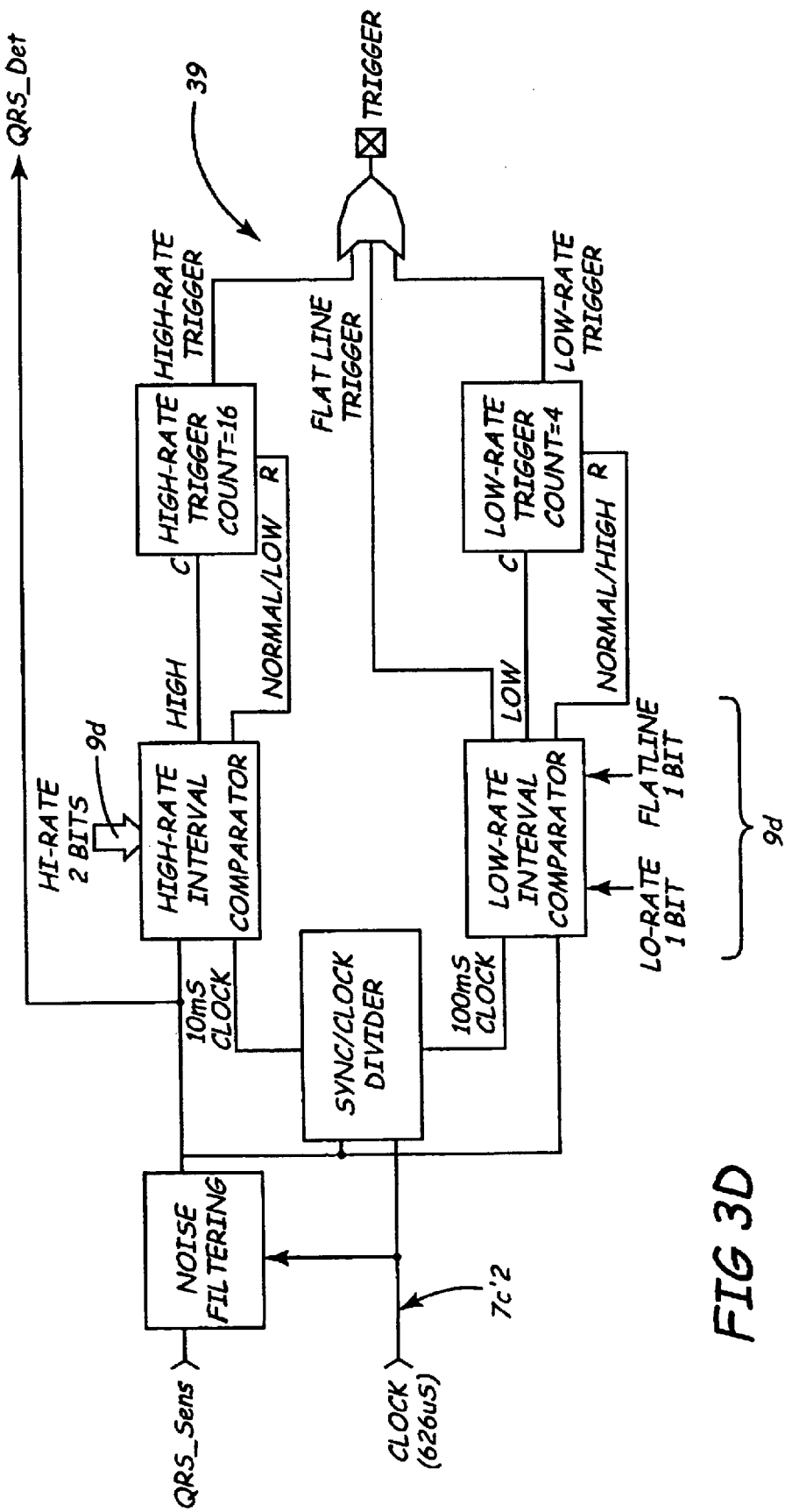

A simple arrhythmia detection circuit 39 is included with this preferred embodiment, and illustrated in FIG. 3D. The output from circuit 36 is monitored at a noise filtering circuit (in our preferred embodiment described in more detail in co-pending application Ser. No. 09/353,167 (now U.S. Pat. No. 6,236,882) filed on even date herewith and again incorporated by this reference setting off a 180 mS accommodation period, but any suitable filtering technique can be used), controlled by a clock input 7c'2. In the preferred embodiment, a high rate can be selected amongst four possible high rate triggers, with two selection bits dedicated to do so at input 9d and the low and flat-line trigger rates each have one bit to turn them on or off provided by inputs 9d. These inputs designated 9d preferably come from a register that holds the gain the mode and the rate settings, illustrated as register 9 in FIG. 3. Such features may be programmable through communication with the implanted device by an external device. One preferred timing for the high rate triggers is 140, 162 and 182 beats per minute, requiring 8 consecutive beats at such a rate to initiate the trigger. Currently we prefer 7 different physician selectable triggers for tachyarrhythmia and 16 consecutive beats at the selected rate, but there is room for variation in these choices. Additionally the trigger may be programmed off. The low rate counter/comparitor may be programmable to detect low rates of 40 or 30 bpm, requiring 4 consecutive low rate intervals to trigger. Additionally a flat-line trigger can be set to occur after 3 or 4 and one half seconds of no QRS detection.

For embodiments that include more sensors and/or electronics, an additional sensor could be added to benefit the patient. One particularly useful would be an activity sensor based on a single or multi-axis accelerometer, which indicates the level of patient activity and his orientation. By checking for output that indicates the occurrence of a VVS (VasoVagal Syncope) episode, (for example, the patient falling from an episode) such an addition offers an improved trigger for events that might otherwise be missed by an arrhythmia detector set up like in FIG. 3D. Such a sensor trigger could replace the circuitry of FIG. 3D.

Additional circuitry and sensors can be provided to determine the presence of Electronic Article Surveillance (called EAS, which is used to protect stores from shoplifting and to provide theft deterrence), EMG, EMI, pacing spikes, defibrillator pulses, edema, pressure, temperature, cardiac output, blood flow, Oxygen saturation of the blood, pH, ischemia in the heart, and so forth, sensors and interpretive circuitry for all of which are presently known, as well as for long term sensing of chemical markers when such sensors become available. The output from any of these sensors and any in combination may be used to trigger ECG storage, storage of data from the sensor itself or just markers indicating which sensor tripped the trigger for ECG storage, as desirable in any particular situation.

Additional circuits may also provided to support additional functions if desired, however in order to reduce size and power consumption and extend the life of the device and reduce the intrusion into the body of the wearer, such auxiliary circuits should be kept to a minimum. Such additional circuits could support oxygen sensing, pressure sensing, respiration sensing, and any other kind of sensing that can be demonstrated to have been known for implanted devices. They may each have their own auto-triggers based on sensor output, or depend on manual triggers. Additionally, activity sensing or positional sensing devices can provide additional input for recording and or auto-triggering functions. As new sensors become available they may also be incorporated into these designs.

Of course the inventive features described herein can be incorporated into a pacemaker or ICD or other therapy delivering device, employing therapy delivering features of such devices in conjunction with the data recording features of this invention.

Storing Noise and Trigger Data in ECG

Figure 5:
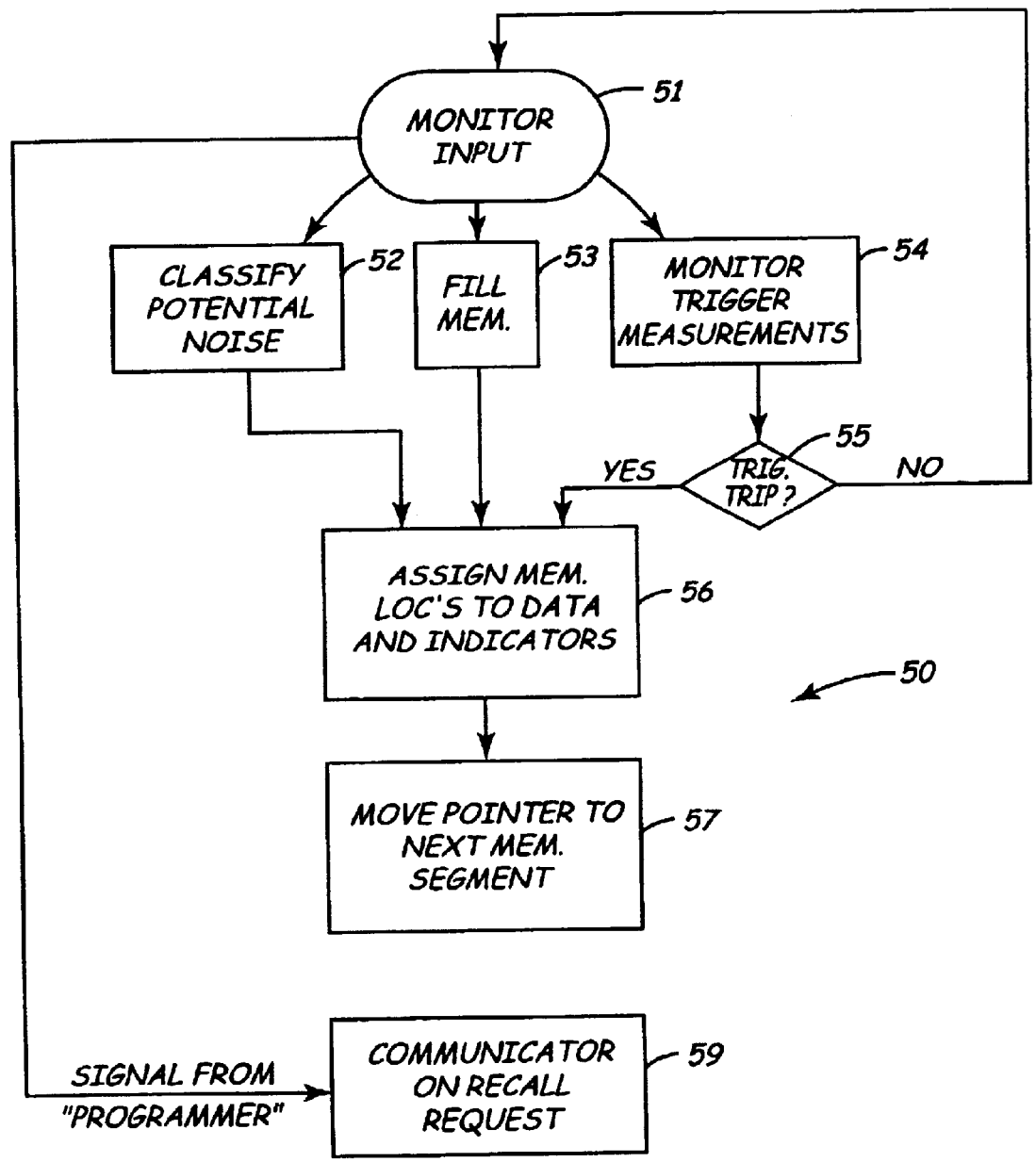
FIG. 5 is a flow chart of a preferred embodiment of the process taught herein.

A simple flow chart 50 identified in FIG. 5 will assist in identifying the process by which indicator flags or markers may be included in electrogram data in the memory of the implanted medical device. The implanted medical device, in the preferred embodiment a looping memory electrogram (ECG) storage system continually monitors the electrogram input in step 51. As it is monitoring this input it also classifying potential noise, step 52, filling the memory with the current ECG step 53, and monitoring the trigger measurements to determine weather an automatic trigger or a patient activated trigger has been tripped. If it is determined that no trigger has been tripped, step 55, the memory can continue to fill and overwrite itself, step 53, and a potential noise classification can continue forward. If however, the trigger has been tripped or a patient activated trigger has been set, memory locations become assigned to the ECG data and to whatever indicators will be used in this particular embodiment indicating the nature of the noise present or the kind of trigger which was activated that caused this section of memory to be filled. This of course occurs in step 56. In step 57, that piece of memory that has been filled up and recorded with electrogram and trigger data as well as possibly noise data, is locked off by moving a pointer to the next memory section in step 57 and the monitoring process begins anew.

It should be noted with regard to step 56 that there is an upper limit to how much data can reasonably be included in an ECG signal without completely degrading that signal and making it unusable, as well as a reasonable range of amounts of supplemental data that can be included before minimal noticeable degradation takes place. In preferred embodiments, we would not suggest including markers in ECG data more than once per heart beat of real time sampling, where the sampling or measuring of the ECG data is taken at 10 mS intervals. (Other timing such as once per second could be used as an alternate limit, and current we are using only one data byte per stored ECG segment which may be several minutes in length). At such a once per beat limit, the system would have available a marker data unit at a rate of 180 beats per minute of one data marker per heart beat, or data marker per 30 ECG samples. Reasonable variation on these figures will be apparent to one of skill in this art and within the ambit of this disclosure. In our current embodiments we limit the inserted data to once per recorded ECG six minute snippet, well within the range of reasonable reconstruction we are describing in this paragraph.

If this process is used in the context of a system an additional step 59 will transfer the memory to an external device and the external device (such as a programmer or other receiver/transceiver near the patient or some other device linked to it which may be remote) will decode and display it.

Figure 6:
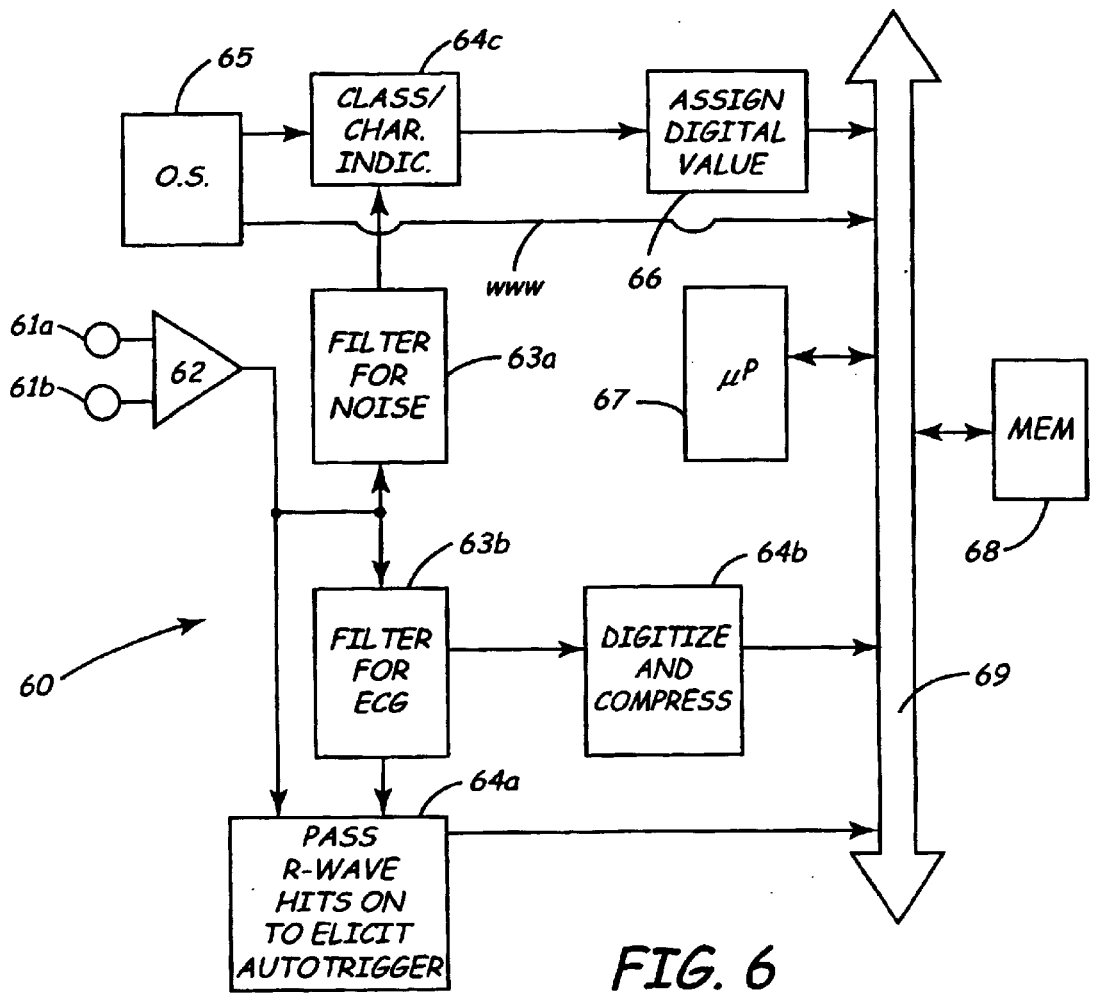
FIG. 6 is a heuristic block diagram illustrating a preferred embodiment.

In FIG. 6, a recharacterization of the functional blocks of the prior FIGS. 3 and 4 is made in diagram 60. Again, the electrodes 61a and 61b provide signals to the input amplifier 62 which will have the electrocardiogram or ECG signal in it. Various kinds of filtering schemes may be required for different purposes. Here two filter circuits are indicated as filters for noise 63a and filters for ECG 63b.

In circuit box 64c the classification or characterization of the indication is made based on the input from the noise filters 63a, also on and input from other sensors if other sensors are included in the device from box 65. A digital value is assigned to the appropriate or highest priority trigger or noise signal from box 64c in box 66. This is then provided to the microprocessor controlled by a program in memory 68 to do with what is required. The filter for the ECG, box 63b, may remove unwanted noise from the ECG signal which can be filtered out according to which ever preferred ECG filtering scheme is appropriate to the particular implantable medical device. For subcutaneous monitoring we prefer the system as described in the co-pending application no. [filed on even date herewith] (P-8789), hereby incorporated by this reference. The filtered signal will be digitized and compressed if preferred in blocks 64b and provided to the data block 69 in this embodiment. The filtered ECG signal and the raw data signal may be also processed by box 64a which passes R-wave hits as an indicator to illicit auto-triggering based on number of hits per second translated into a heart beat rate which inaccurate to for the patient. Details of such triggers are plentiful in the prior art and a preferred system is described in the aforementioned co-pending patent application incorporated herein by reference in its entirety.

Although separate memory elements such as ROMs, or separate RAM memory elements could provide the memory storage to provide the programming for the microprocessor 67, it is appropriate for the sake of simplicity to think of the programming as being stored in the same memory 68 into which the digitized and compressed ECG data will be stored to simplify the explanation of a device. Any conventional memory arrangement may be used.

In our preferred embodiment, we store sampled amplitude readings of the electrogram signal, but employ a lossy compression scheme whereby some amplitude measurements made are stored and some intervening measurements are not. A description of an appropriate scheme for the compression of ECG data in our preferred embodiment is described in U.S. Pat. No. 5,331,966 hereby incorporated by reference.

Figure 7:
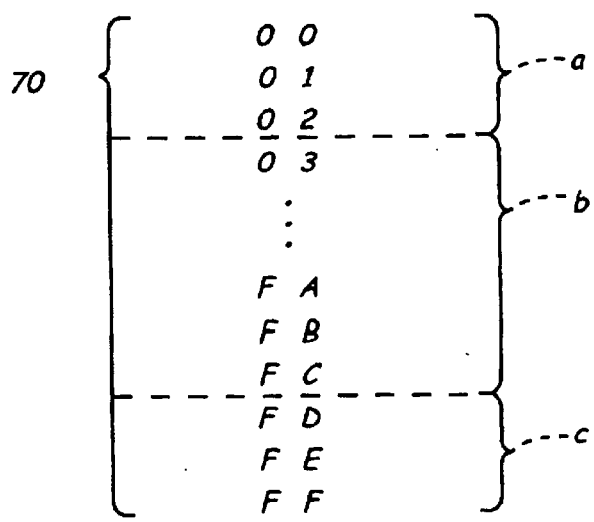
FIG. 7 is a number chart.

Referring briefly to FIG. 7, in the preferred embodiment a 256 level amplitude indication may be presented as a single byte of data. Here the range of byte of data is indicated in area 70. The very lowest amplitudes 00(hex) –02(hex) (a) is the very far low of the input amplifiers' range. Likewise the upper end of the range is at area (c). Accordingly, by retaining only the middle range (b) as good data and blocking off the far end data (located at end ranges 'a' and 'b') we have effectively established a range of codes (those in areas 'a' and 'b') that may be used to indicate other things besides the amplitude of the ECG signal in the very same space that the ECG signal is being recorded in memory.

There are several reasons for choosing the upper end and lower ends of the available range of data, perhaps the most important ones being that not much useful data is in the height of the QRS wave, and that there is a lack of complexity in the design requirements to exclude these values as available outputs from the A/D (Analog to Digital) converter circuit, thus avoiding some kind of digital filter before the storage of data to memory. The isoelectric or near zero values of the ECG could also provide values of use to recording information other than the ECG in the ECG data storage area, but as just mentioned this is not preferred since it will require some complexity in designing the circuitry and data to memory storage function.

Figure 10:
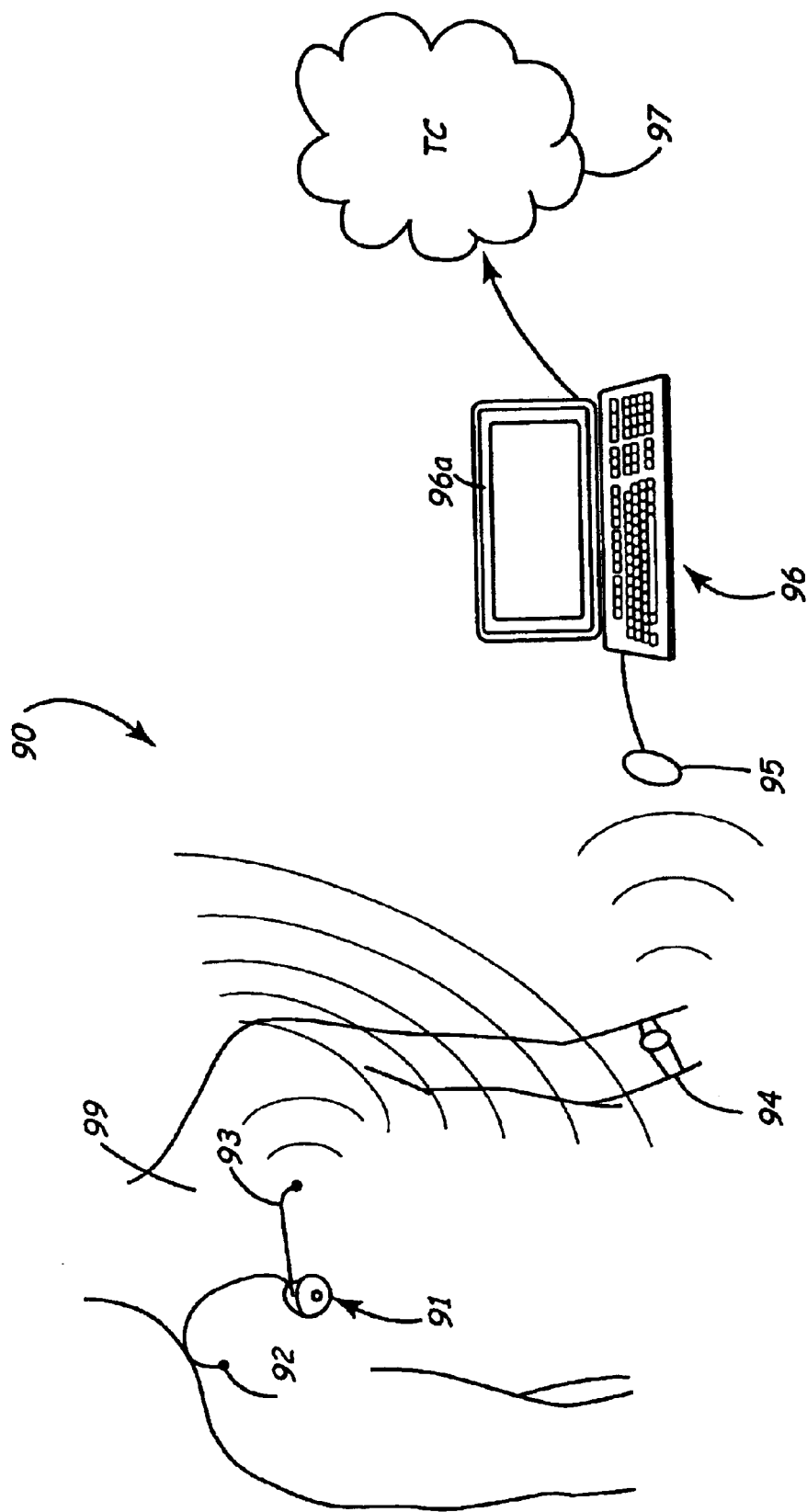
FIG. 10 is a heuristic illustration of a system for use by a preferred embodiment.

In FIG. 10, an electrogram recording implanted medical device 91 which may have leads containing electrodes 92 as well as antenna leads 93 can be seen in a system 90 which provides for communication between the implanted medical device 91 and external devices 94, 96 and a telecommunication system 97. Here a device like device 94, which is worn on or carried by the patient, can be a repeater for providing additional range to the telemetry signal from device 91 through an antenna or lead acting as an antenna 93 or the device 91 communicate with device 96 through an antenna 95 attached to the external device 96. Most commonly this external device is called a "programmer." In any event, in order for the device 96 to interrupt correctly a stream of data having amplitude information within it, it is preferred that some of the available byte values at the far ends of the byte value range may be set aside for communicating information other than ECG amplitude values.

Figure 13:
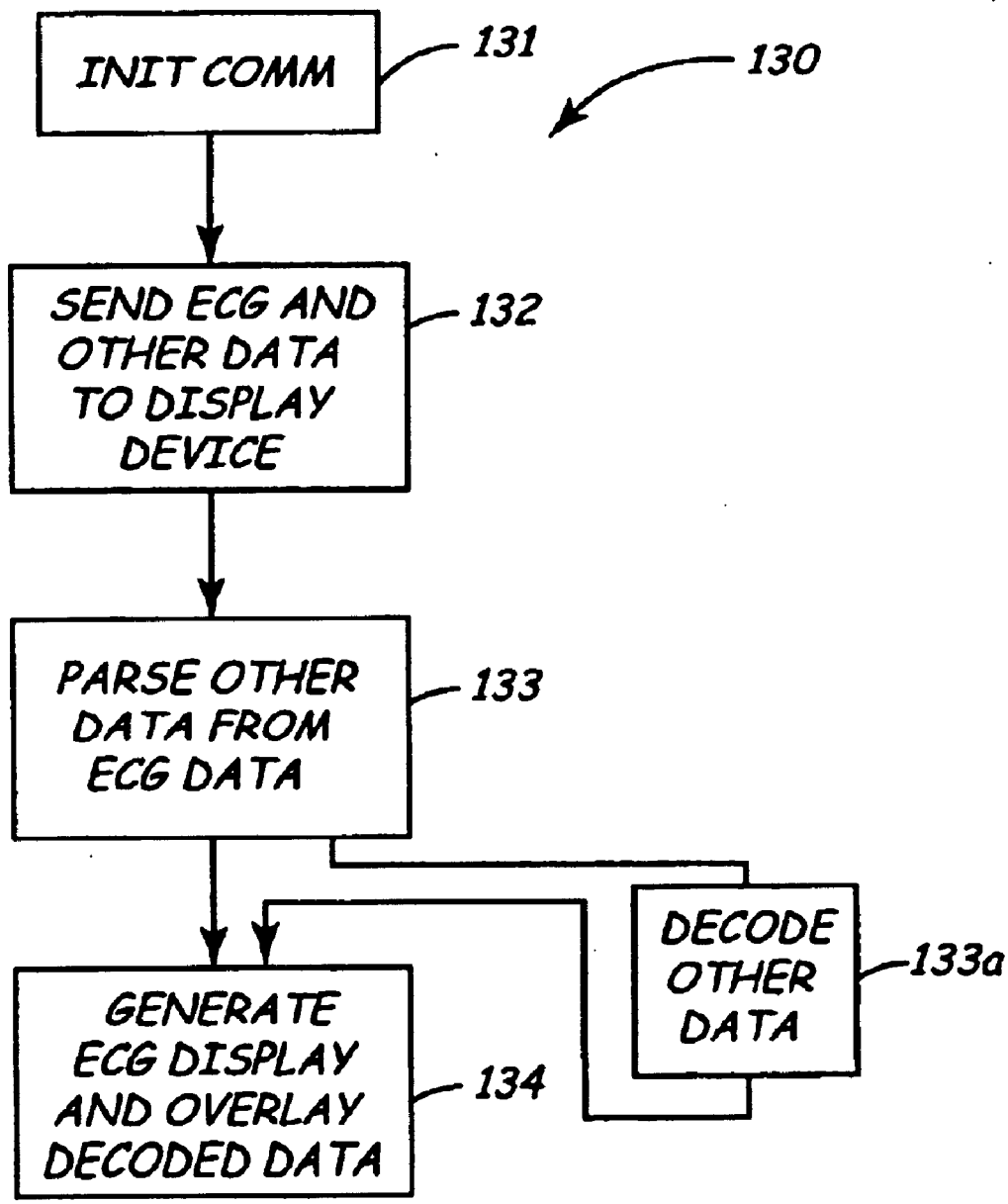
FIG. 13 is a flow chart of the process of transforming a data marker indicator signal into a display feature in accord with this invention.

The flow of data from the memory of the IMD to the display screen 96a of the programmer, or another device receiving the data (which may even be downstream in the telecommunications network 97) is explained with reference to FIG. 13, via the flow chart 130. First, of course communications must be initiated 131, and the implanted device must communicate the ECG and other (marker or indicator or other sensor) data to the external device(s) in step 132. There must be a program in the external device that parses the other data from the ECG data in step 133 and it must also then be decoded into the display icon or other display artifact appropriate to the other data (step 133a). Preferably, the external device will then generate a display of the ECG with the other data displayed with it similarly to the display shown in FIGS. 8A–9B, or in similar useful manner. For an example of a useful display, consider that if a pressure wave signal is recorded simultaneously with the ECG, they could be displayed with temporal alignment in the same window or in two aligned windows. Various iconic representations for types of noise, types of auto-triggers are easily imagined within the ambit this invention's teachings.

Of course, the external device will preferably have a program feature to be able to visually clean up the ECG signal by not displaying the other data if desired, an dto print the ECG in any form desired.

Figure 9A:
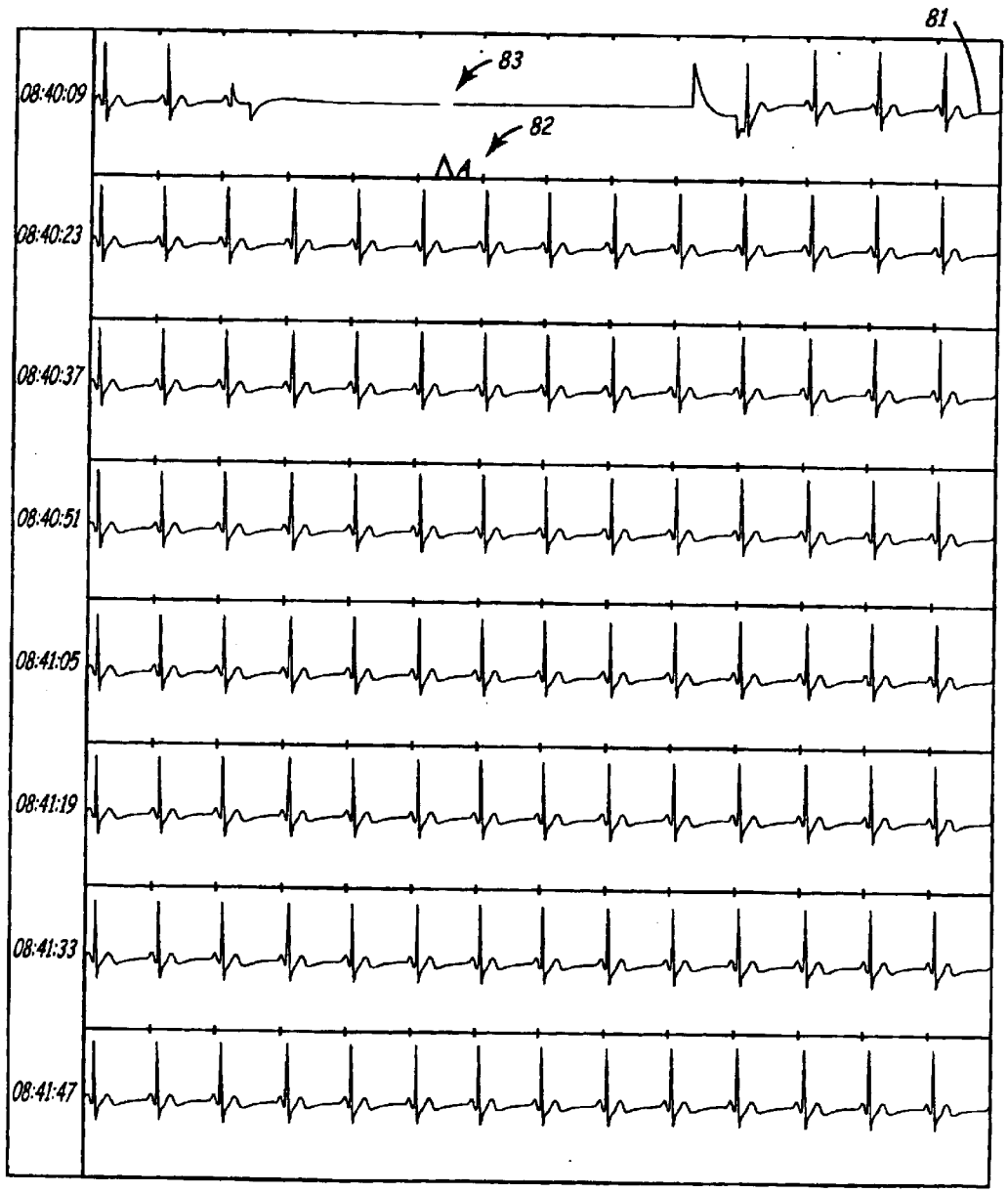
FIGS. 9A and 9B are rough representations of displays of an ECG segment for use with a preferred embodiment.
Figure 9B:
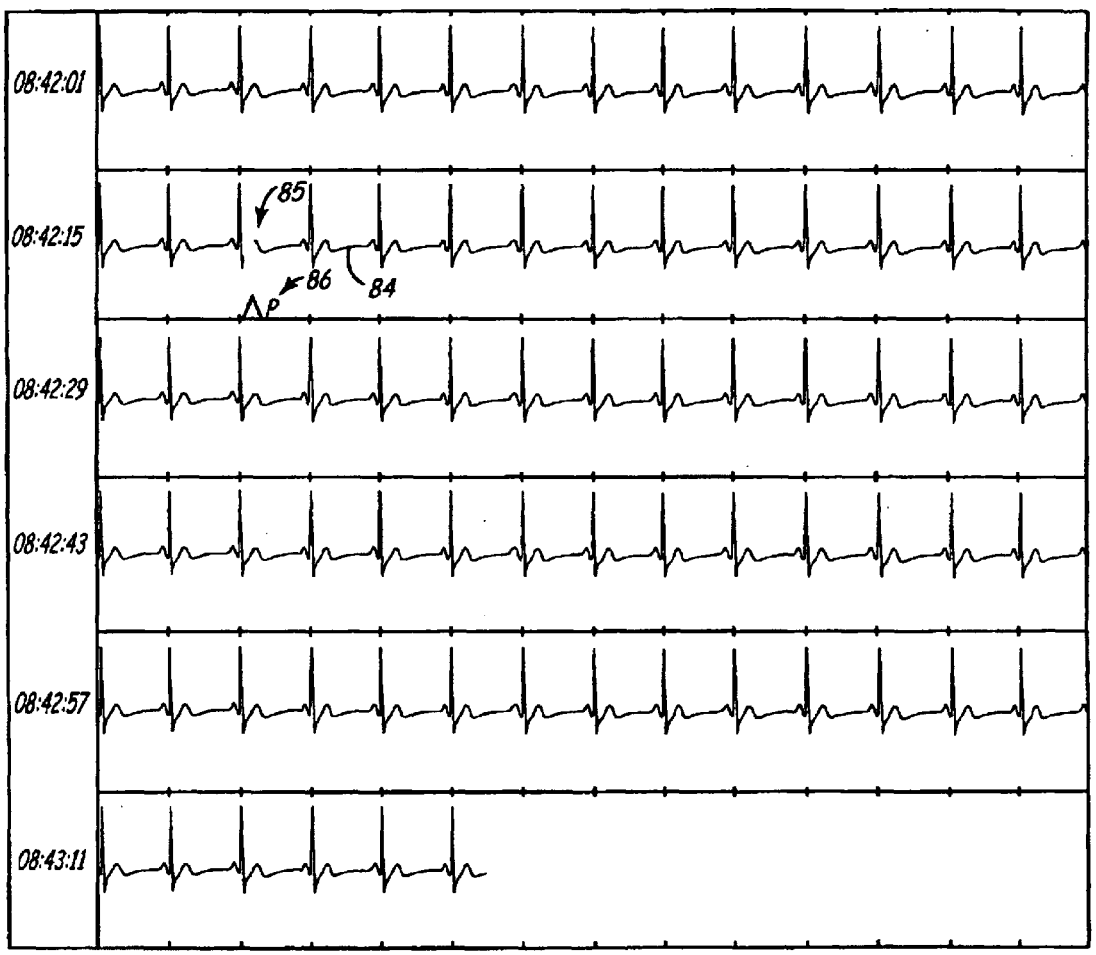

Thus, as a simple example, where only indications of automatic activation or manual activation are shown on a display on a device such as programmer 96, values 00 (hex) and FF (hex) will indicate an automatic activation or a manual or patient activation. Thus, in FIG. 9a, the programmer 96 will draw on its screen from the sampled of electrogram signals an image of a electrocardiogram like 86 possibly with a break at 83 where the indicator of the automatic trigger 82 replaces some of the data. An intelligent interpolating program could fill the gap at 93 if desired. In FIG. 9b, a patient activation will be shown by the mark at 86 in line 86 again with a gap at point 85.

Figure 8A:
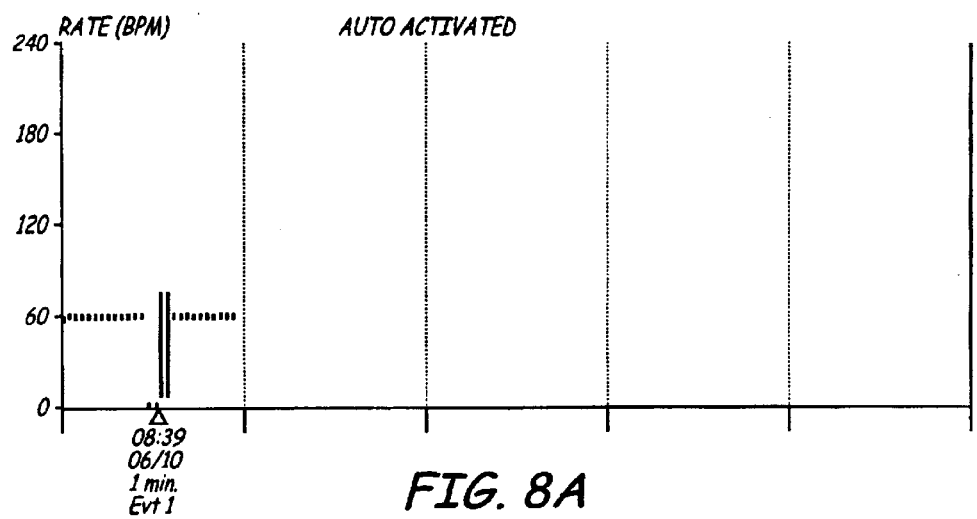
FIGS. 8A and 8B are rough representations of displays for use with a preferred embodiment.
Figure 8B:
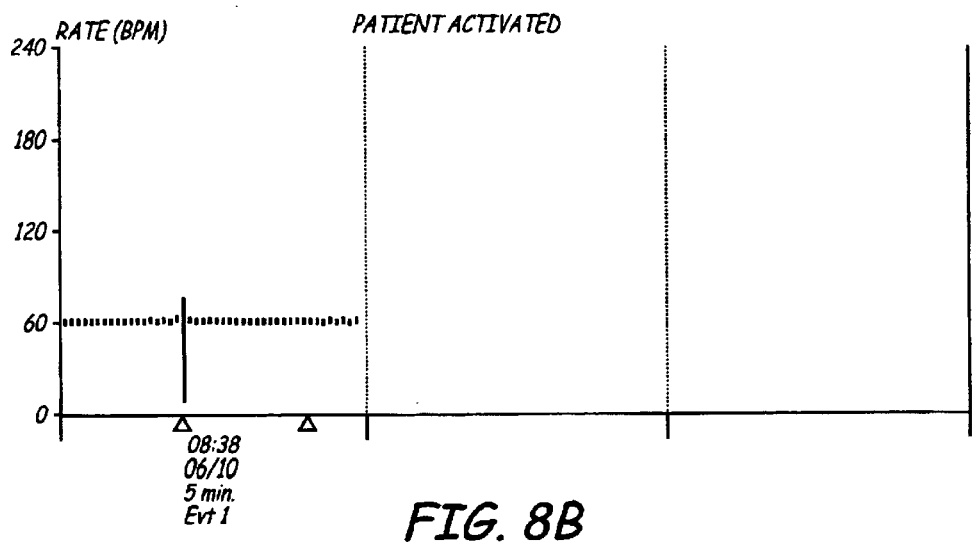

For convenience of the physician or other person reviewing the data, a long term rate graph can also be drawn as in illustrated in FIGS. 8a and 8b. Here, the position and height of the bars indicate the range of heart rate for the particular time of the bar, and the arrows indicate the automatic triggers.

Using more than just FF and 00 (say 00, 01, 02 and FA–FF) provides a larger number of disallowed (unavailable) for amplitude values which can then be used to provide indications of other types of useful information for interpreting the data such as, particular kinds of noise, particular out of range sensor conditions or an exact identifier for the particular type of arrhythmia or other auto-trigger which caused a particular segment of ECG to be stored.

ECG Recording Functionality for Preferred Embodiments.

The most important function of the simple versions of this invention is the long term electrocardiogram (ECG) monitoring of the subcutaneous (or intramuscular) ECG. The device continuously records and monitors the subcutaneous ECG in an endless loop of memory. In its primary mode the device is triggered by the patient to save/retain in memory a prior period of a few minutes or seconds of ECG data after the patient feels symptoms of interest (e.g. syncope, palpitations, etc.), plus some period of time after the patient activation of the patient trigger. (Patient activation can be done with a small device that signals the implantable device from outside the body, a commonly understood idea, disclosed in some detail in co-pending U.S. application Ser. No. 09/033,678, incorporated herein by this reference.)

In the preferred embodiment with 128K of memory the device can store 42 or 21 minutes of ECG, which can be reset after off-loading by telemetry to an external device for analysis and display. In one form there are four modes settable for the patient to trigger activation of data storage recording, only and in another form there are auto-triggers which automatically trigger the storage of data. (The data stored may include the ECG and any additional data also, as described in this document). In the patient only (also called "manual") trigger modes, the patient can capture either one or three events between off-loadings at either no compression or at a compression ratio of 1:2 or some other device supported compression ratio. When setting the mode of the implant, the physician or attendant can decide whether to record data in a compressed mode or not in the preferred embodiment. If greater detail of the triggered ECG is required than can be developed from compressed data storage, the physician can select non-compressed recording, thereby reducing the time available to record. In some embodiments sample rate may be modified as well, but this is not preferred.

Compression is preferably done using a known compression algorithm implemented in hardware. Many types are known and software compression could be used if desired too. An excellent and easy to implement example, which shows a constant data-independent compression scheme, is found in the article "Arrhythmia Detection Program for an Ambulatory ECG Monitor" by Mueller, copyright 1978, ISA, ISBN 876645. Using this algorithm in one embodiment we have used a pre-trigger time of record of a maximum of 2400 seconds and a maximum post trigger record of 120 seconds, and at the higher sampled or less compressed rate of 1200/60 for a single event and 360/60 seconds for three events.

These time values are obviously only examples and the reader can set whatever time he or his physician feels is appropriate within the ambit of this invention. After such a record is made the device memory locations are full and will be overwritten by the next triggered event since in the preferred embodiment the memory is maintained in a continuous loop.

An implantable medical device with the invention may have several operating modes including pure auto-triggering, patient triggered only modes, and combination modes, if desired. It should be considered that with auto-triggered events, the determination by the device of an event worth recording and the subsequent activation of the trigger by the device itself will be faster than the patient finding his device for activation or otherwise activating the device, so the pre trigger time record for automatic triggered storage sequences or ECG segments can be smaller. In one preferred embodiment the memory is segmented to allow for 14 auto-triggers and 3 manual triggers. Further detail regarding modes is described with reference to FIGS. 11 and 12.

The patient activated triggering of a preserved form of the recorded ECG signal can be carried out by using a small hand-held external device which may be of any number of different forms. A first way is through a hand-held battery-powered device which uses a coded radio-frequency telemetered signal through the skin to the device, on the press of a button. A simpler device a small hand-held used to close a magnetic switch within the implanted device to trigger it by holding the magnet close or patting the area of the body that has the implant a set number of times with the magnet. Other methods for triggering ECG data retention in memory (each of which has it's own advantages for implementation) are to use physical tapping or slapping of the finger or hand on the skin over the device in a particular cadence and/or number of taps (advantage is that no triggering device is needed. With such methods the disadvantage is that the patient needs to memorize the triggering sequence. Matched voice activation with a known command is possible but the complexity at this time of discerning voice commands precludes such activation for the present time, but could be in future devices using this invention. Another approach is light activation through the skin using a light source and receiver, auditory/sonic activation using a hand-held auditory/sonic source held over the skin with a microphone receiver in the device. All these methods are patient activated and require patient compliance or cooperation, a feature this device was designed to avoid. Accordingly in conjunction with one of these patient triggers or alone, an automatic activation or trigger for holding a chunk of memory should be included. This could be activated by automatic recognition of an arrhythmia, a heartbeat too fast or too slow, or for any other condition the device may be set up to find.

If a patient trigger is used it is advantageous provide feedback to the patient regarding whether the attempt to trigger long term storage of the event was successful. To accomplish this the implant should telemeter out a signal that indicates it has recognized a valid trigger. (This of course requires additional circuitry and usage of the limited available power supply.) The external triggering device then notifies the patient via the triggering device or through some known alarm mechanism whether they have or have not properly triggered the implanted device. This notification can be one of any combination of a number of feedback methods including: one or two visual sources such LED's, an auditory source such as a beeping speaker in one or two tones, or a tactile source such as a vibration. See also U.S. Pat. No. 5,518,001 (incorporated herein by this reference) for other potential trigger-indicator ideas for a hand-held patient activated trigger device.

Features and Construction of the Preferred Embodiment Implantable Devices.

Figure 11:
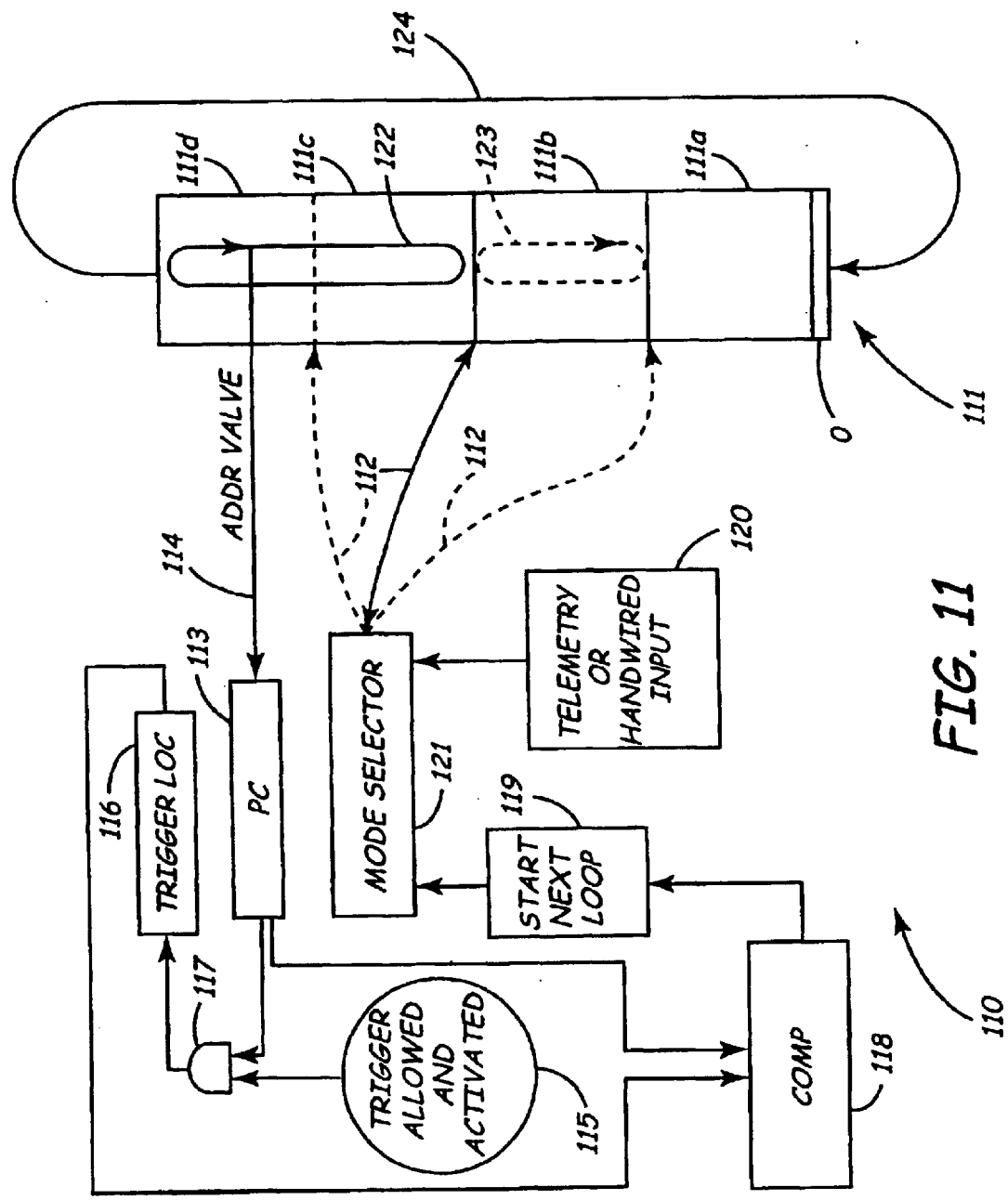
FIG. 11 is a block diagram of the looping memory and its control circuitry in accord with a preferred embodiment of the invention.

Referring now to FIG. 11 in which a block diagram of a functional model 110 of the controller and memory 111 of a preferred embodiment device is illustrated. The memory is generally organized as a continuous loop of, preferably, 8 bit addresses starting at address 0 and looping back around to address 0 through line 124. By telemetry or hard-wired input during manufacture 120, a mode selector 121 is set so as to divide the memory 111 into working segments 111a–d. The address of the start of each of these segments is indicated with lines 112.

Since this device is used for recording physiologic data, after the data is compressed, converted, formatted and is in appropriate digital form, it is continually recorded in the memory 111. The address value at the tip of arrow 122 in the combined memory space 111d, 111c is monitored by a program counter register 113.

The size of each memory segment set in a given mode limits the amount of data available for each triggered event. In the preferred embodiment, using only one program counter set of registers, the flexibility to accommodate two different trigger lengths can be limited. Alternate forms of memory allocation are available. For example organizing the entire looping memory as one unit and marking each trigger would allow more flexibility but increase the overhead. See for example the memory structure in Enigra, U.S. Pat. No. 5,339,824, FIG. 7, (the patent being incorporated herein by this reference in its entirety.

To use a single program counter the actual trigger address minus the time (in memory location storage events) required to have already stored the amount of data needed for pre event analysis for that trigger is stored as a value in the trigger location register 116 of FIG. 11. If a larger time for pre trigger recording is required by a trigger occurring during an already triggered event,(say, a manual trigger follows the occurrence of an auto-trigger), the value in the trigger register can be decrement, thus yielding a larger pre trigger time period in the allocated memory segment for this event. A priority system for whether to extend the pre trigger record is simple to implement but again would require additional hardware and is not preferred. In fact the simplest construction ignores any new triggers once a trigger is set until the results of comparing the program counter with the trigger register corresponds to a match in value.

It is preferred to save more data for a manual triggered event than an auto-triggered one because upon recovering from an event the patient has enough time to recover, get their wits about them, and find the triggering device. Manual triggering may therefore be set to record in double or multiple sized segments. FIG. 11's segments 111c and d are joined by looping arrow 122 to give effect to this concept.

Because the memory size is preferably quite limited a time record or first-in-first-out pool record should be kept so that that the newest triggers record only over the oldest events segments. An additional preferred feature allows for a mode that prevents recording over any triggered event segment. This is preferably implemented by a counter which increments for each segment used and has limit for the set number of available looping segments. When this counter reaches its limit, recording of new events stops.

When a trigger is activated and under the control program of the device is allowed, a signal 115 is permitted by some control gate 117 to allow the program counter address to be loaded into a trigger location address register 116. After loading, each subsequent clock cycle or set of clock cycles depending on the configuration of the device will load the trigger location from 116 into a comparator 118 to compare this location with the program counter address stored in register 113. When comparator 118 finds that they match, an appropriate output is generated to start the next loop via control circuit 119. This control circuit 119 will cause the mode selector to point to the next available loop location effectively placing that into the program counter 113.

Figure 12:
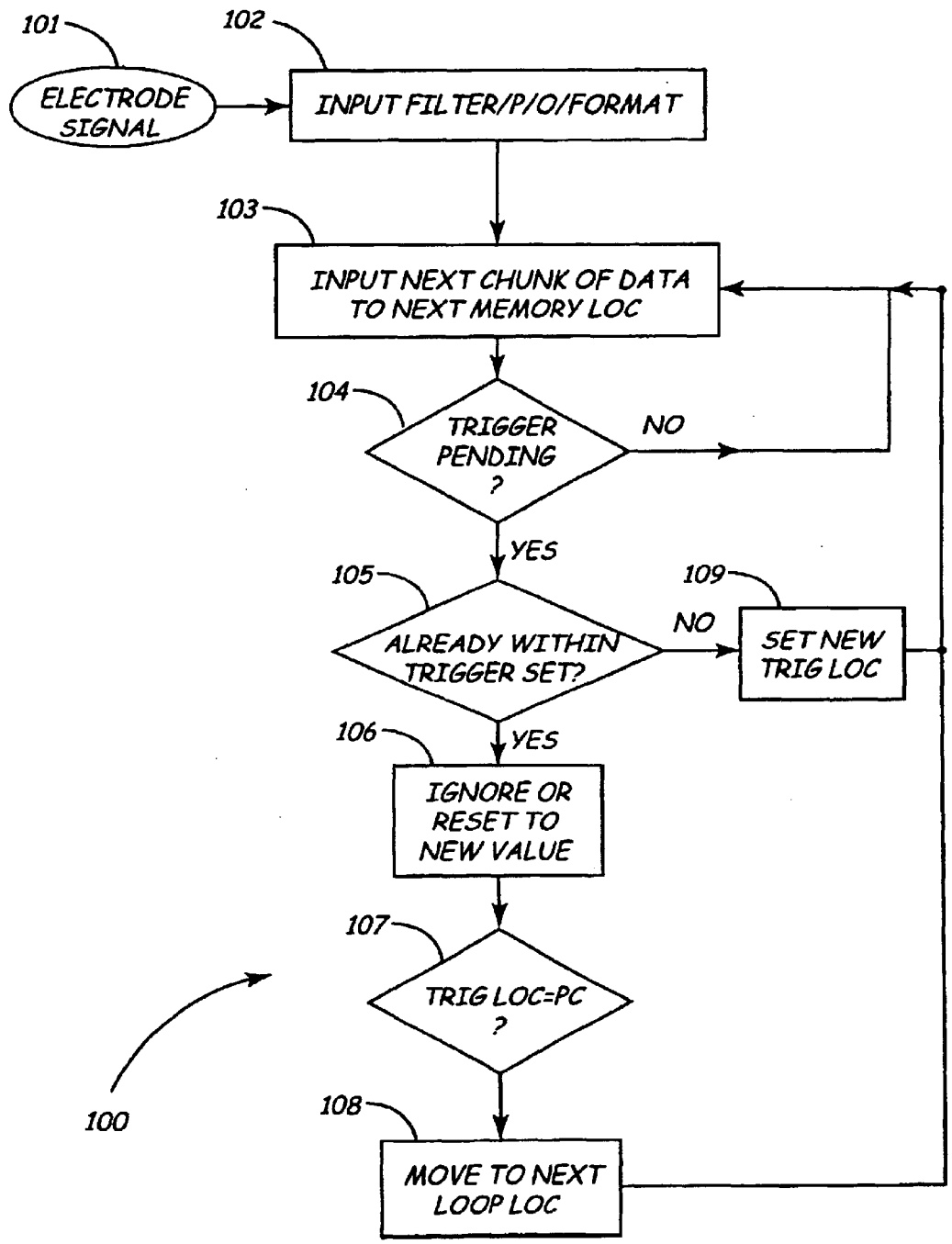
FIG. 12 is a flow chart of the functioning of the recordation of triggered events in a preferred embodiment of the invention.

The diagrammatic algorithm 100 to indicate the flow of this information is found in the illustration of FIG. 12 in which an electrode signal 101 is input filtered, converted from analog input to digital values, compressed and formatted if desired in step 102 so as to be in appropriate form to store in a memory location designated by a program counter pointer.

This data word's form could be containing a value representing input signal compressed at various available ratios, and may be mixed with other information like data provided by another sensor or clock data. The data stored will of course carry information related to the signal taken at the sampling rate. Thus lower sampling rates to save power will adversely affect the usefulness or detail of the data. Whatever its preferred form, each data point stored as a word is referred to as a chunk.

Output form step 102 provides the next chunk of data to the next memory location in step 103.

Device checks to see if there is any trigger pending after storing each chunk of data in step 104. If not, the next chunk of data is stored. If there is, the device preferably checks to see if there is another trigger already set and if so either ignores it or resets the value of the reserved looping memory area (like areas 111a–d in FIG. 11) to accommodate a larger trigger or it ignores the trigger if it is smaller or if it indicates a smaller value needs to be stored. If on the other hand, no trigger is already set, then a new trigger location is recorded in the trigger location memory and then the next memory location is written with the next chunk of data. At step 107 if the trigger location is equal in value to the program counter, the device knows that it has gone through the entire loop reserved by the mode selector for this particular event record and then moves on to the next loop location, step 108.

It should be recognized that any of the inventive concepts taught herein may be applied to implantable devices to supplement their other functions, such as a supplemental recording system for a pacemaker, implantable drug pump, et cetera. Further, known enhancements to telemetric communication can be used to automatically activate off-loading of data to a device located in the patient's home. Such a device could send its received communications to the attending care giver/physician's office at some convenient time, telephonically or otherwise so as to enable close compliance with prescribed follow-up of patient conditions. This invention is not understood to be limited in scope except by the following claims.

What is claimed is:

1. A method comprising:
   monitoring an electrogram signal to find a trigger event in the electrogram signal, wherein said electrogram signal is obtained via at least a pair of subcutaneous electrodes spaced from a heart;
   generating a trigger indicator signal upon finding the trigger event;
   recording a plurality of sampled values of the electrogram signal in a memory structure; and
   recording the trigger indicator signal in the memory structure contemporaneously with the recording of the sampled values of the electrogram signal,
   wherein recording the trigger indicator signal in the memory structure comprises replacing one of the sampled values with the trigger indicator signal and wherein the trigger event comprises detection of out-of-range values of the electrogram signal.

2. A method according to claim 1, wherein the trigger indicator signal is a first trigger indicator signal corresponding to a first trigger event, the method further comprising:
   generating a second trigger indicator signal upon finding the second trigger event in the electrogram signal; and
   recording the second trigger indicator signal in the memory structure contemporaneously with the recording of the sampled values of the electrogram signal.

3. A method according to claim 1, further comprising compressing the plurality of sampled values prior to recording the plurality of sampled values in the memory structure.

4. A method according to claim 1, further comprising:
   transmitting the recorded sampled values of the electrogram signal and the recorded trigger indicator signal to an external device;
   parsing the trigger indicator signal from the recorded sampled values of the electrogram signal; and
   generating a display as a function of the recorded sampled values.

5. A method according to claim 4, wherein generating the display as a function of the recorded sampled values comprises displaying an electrogram waveform.

6. A method according to claim 4, further comprising generating the display as a function of the trigger indicator signal.

7. A method according to claim 6, wherein generating the display as a function of the trigger indicator signal comprises generating a display icon as a function of the trigger indicator signal.

8. A method according to claim 6, further comprising:
   monitoring the electrogram signal to find noise in the electrogram signal;
   generating a noise indicator signal upon finding the noise, the noise indicator signal being a function of the noise found in the electrogram signal; and
   recording the noise indicator signal in the memory structure contemporaneously with the recording of the sampled values of the electrogram signal,
   wherein recording the noise indicator signal in the memory structure comprises replacing another of the sampled values with the noise indicator signal.

9. A method according to claim 8, further comprising:
   transmitting the recorded noise indicator signal to an external device; parsing said noise indicator signal from the recorded sampled values of the electrogram signal; and
   generating a second display as a function of the recorded sampled values.

10. A method according to claim 9, further comprising generating the display as a function of the noise indicator signal.

11. A method according to claim 10, wherein generating the display as a function of the noise indicator signal comprises generating a display icon as a function of the noise indicator signal.

12. A method according to claim 1, further comprising recording other sensor data in the memory structure.

13. A method according to claim 1, wherein monitoring the electrogram signal to find a trigger event in the electrogram signal comprises monitoring the electrogram signal to find a predetermined pattern in the electrogram signal.

14. A method, comprising:
    monitoring an electrogram signal to find a trigger event in the electrogram signal, wherein said electrogram signal is obtained via at least a pair of subcutaneous electrodes spaced from a heart;
    generating a trigger indicator signal upon finding the trigger event;
    recording a plurality of sampled values of the electrogram signal in a memory structure; and
    recording the trigger indicator signal in the memory structure contemporaneously with the recording of the sampled values of the electrogram signal,
    wherein recording the trigger indicator signal in the memory structure comprises replacing one of the sampled values with the trigger indicator signal, and further comprising recording other sensor data in the memory structure, wherein the other sensor data comprises a plurality of samples of other sensor data, the method further comprising recording one sample of other sensor data per thirty sampled values of the electrogram signal.

15. A medium containing stored executable instructions for performing a method, comprising:
    instruction for monitoring an electrogram signal to find a trigger event in the electrogram signal, wherein said electrogram signal is obtained via at least a pair of subcutaneous electrodes spaced from a heart;

instructions for generating a trigger indicator signal upon finding the trigger event;

instructions for recording a plurality of sampled values of the electrogram signal in a memory structure; and instructions for recording the trigger indicator signal in the memory structure contemporaneously with the recording of the sampled values of the electrogram signal, wherein the recording the trigger indicator signal in the memory structure further comprises instructions for replacing one of the sampled values with the trigger indicator signal and wherein the trigger event comprises detection of out-of-range values of the electrogram signal.

16. A medium according to claim 15, wherein the trigger indicator signal comprises a first trigger indicator signal corresponding to a first trigger event, and further comprising:

instructions for generating a second trigger indicator signal upon finding the second trigger event in the electrogram signal; and instructions for recording the second trigger indicator signal in the memory structure contemporaneously with the recording of the sampled values of the electrogram signal.

17. A medium according to claim 15, further comprising instructions for compressing the plurality of sampled values prior to recording the plurality of sampled values in the memory structure.

18. A medium according to claim 15, further comprising:

instructions for transmitting the recorded sampled values of the electrogram signal and the recorded trigger indicator signal to an external device;

instructions for parsing the trigger indicator signal from the recorded sampled values of the electrogram signal; and instructions for generating a display as a function of the recorded sampled values.

19. A medium according to claim 18, wherein the instructions for generating the display as a function of the recorded sampled values comprises instructions for displaying an electrogram waveform.

20. A medium according to claim 18, further comprising instructions for generating the display as a function of the trigger indicator signal.

21. A medium according to claim 20, wherein the instructions for generating the display as a function of the trigger indicator signal further comprises instructions for generating a display icon as a function of the trigger indicator signal.

22. A medium according to claim 20, further comprising:

instructions for monitoring the electrogram signal to find noise in the electrogram signal;

instructions for generating a noise indicator signal upon finding the noise, the noise indicator signal being a function of the noise found in the electrogram signal; and instructions for recording the noise indicator signal in the memory structure contemporaneously with the recording of the sampled values of the electrogram signal, wherein recording the noise indicator signal in the memory structure comprises replacing another of the sampled values with the noise indicator signal.

23. A medium according to claim 22, further comprising:

instructions for transmitting the recorded noise indicator signal to an external device;

instructions for parsing said noise indicator signal from the recorded sampled values of the electrogram signal; and instructions for generating a display as a function of the recorded sampled values.

24. A medium according to claim 23, further comprising instructions for generating the display as a function of the noise indicator signal.

25. A medium according to claim 24, wherein the instructions for generating the display as a function of the noise indicator signal further comprises instructions for generating a display icon as a function of the noise indicator signal.

26. A medium according to claim 15, further comprising instructions for recording other sensor data in the memory structure.

27. A medium according to claim 15, wherein the instructions for monitoring the electrogram signal to find a trigger event in the electrogram signal further comprises instructions for monitoring the electrogram signal to find a predetermined pattern in the electrogram signal.

28. A medium containing stored executable instructions for performing a method, comprising:

instructions for monitoring an electrogram signal to find a trigger event in the electrogram signal, wherein said electrogram signal is obtained via at least a pair of subcutaneous electrodes spaced from a heart;

instructions for generating a trigger indicator signal upon finding the trigger event;

instructions for recording a plurality of sampled values of the electrogram signal in a memory structure; and instructions for recording the trigger indicator signal in the memory structure contemporaneously with recording sampled values of the electrogram signal, wherein the recording the indicator signal in the memory structure further comprises instructions for replacing one of the sampled values with the trigger indicator signal and further comprising instructions for recording other sensor data in the memory structure and wherein the other sensor data comprises a plurality of samples of other sensor data, the medium further comprising instructions for recording one sample of other sensor data per thirty sampled values of the electrogram signal.

29. An apparatus for performing a method, comprising:

means for monitoring an electrogram signal to find a trigger event in the electrogram signal, wherein said electrogram signal is obtained via at least a pair of subcutaneous electrodes spaced from a heart;

means for generating a trigger indicator signal upon finding the trigger event;

means for recording a plurality of sampled values of the electrogram signal in a memory structure; and means for recording the trigger indicator signal in the memory structure contemporaneously with the recording of the sampled values of the electrogram signal, wherein the recording the trigger indicator signal in the memory structure further comprises means for replacing one of the sampled values with the trigger indicator signal and wherein the trigger event comprises detection of out-of-range values of the electrogram signal.

30. An apparatus according to claim 29, wherein the trigger indicator signal comprises a first trigger indicator signal corresponding to a first trigger event, and further comprising:

means for generating a second trigger indicator signal upon finding the second trigger event in the electrogram signal; and means for recording the second trigger indicator signal in the memory structure contemporaneously with the recording of the sampled values of the electrogram signal.

31. An apparatus according to claim 29, further comprising means for compressing the plurality of sampled values prior to recording the plurality of sampled values in the memory structure.

32. An apparatus according to claim 29, further comprising:
   means for transmitting the recorded sampled values of the electrogram signal and the recorded trigger indicator signal to an external device;
   means for parsing the trigger indicator signal from the recorded sampled values of the electrogram signal; and
   means for generating a display as a function of the recorded sampled values.

33. An apparatus according to claim 32, wherein the means for generating the display as a function of the recorded sampled values comprises means for displaying an electrogram waveform.

34. An apparatus according to claim 32, further comprising means for generating the display as a function of the trigger indicator signal.

35. An apparatus according to claim 34, wherein the means for generating the display as a function of the trigger indicator signal further comprises means for generating a display icon as a function of the trigger indicator signal.

36. An apparatus according to claim 34, further comprising:
   means for monitoring the electrogram signal to find noise in the electrogram signal;
   means for generating a noise indicator signal upon finding the noise, the noise indicator signal being a function of the noise found in the electrogram signal; and
   means for recording the noise indicator signal in the memory structure contemporaneously with the recording of the sampled values of the electrogram signal,
   wherein recording the noise indicator signal in the memory structure comprises replacing another of the sampled values with the noise indicator signal.

37. An apparatus according to claim 36, further comprising:
   means for transmitting the recorded noise indicator signal to an external device;
   means for parsing said noise indicator signal from the recorded sampled values of the electrogram signal; and
   means for generating a display as a function of the recorded sampled values.

38. An apparatus according to claim 37, further comprising means for generating the display as a function of the noise indicator signal.

39. An apparatus according to claim 38, wherein the means for generating the display as a function of the noise indicator signal further comprises means for generating a display icon as a function of the noise indicator signal.

40. An apparatus according to claim 29, further comprising means for recording other sensor data in the memory structure.

41. An apparatus according to claim 29, wherein the means for monitoring the electrogram signal to find a trigger event in the electrogram signal further comprises means for monitoring the electrogram signal to find a predetermined pattern in the electrogram signal.

* * * * *